(12) United States Patent
Mehta et al.

(10) Patent No.: US 7,399,779 B2
(45) Date of Patent: *Jul. 15, 2008

(54) 3,6-DISUBSTITUTED AZABICYCLO [3.1.0] HEXANE DERIVATIVES USEFUL AS MUSCARINIC RECEPTOR ANTAGONISTS

(75) Inventors: Anita Mehta, Buffalo Grove, IL (US); Arundutt V. Silamkoti, Secunderabad (IN); Jang Bahadur Gupta, Haryana (IN)

(73) Assignee: Ranbaxy Laboratories Limited, Gurgaon (IN)

( * ) Notice: Subject to any disclaimer, the term of this patent is extended or adjusted under 35 U.S.C. 154(b) by 31 days.

This patent is subject to a terminal disclaimer.

(21) Appl. No.: 10/520,573

(22) PCT Filed: Jul. 8, 2002

(86) PCT No.: PCT/IB02/02663

§ 371 (c)(1),
(2), (4) Date: Feb. 7, 2006

(87) PCT Pub. No.: WO2004/004629

PCT Pub. Date: Jan. 15, 2004

(65) Prior Publication Data

US 2007/0004791 A1    Jan. 4, 2007

(51) Int. Cl.
    A61K 31/403    (2006.01)
    C07D 209/52    (2006.01)
(52) U.S. Cl. ....................... 514/412; 548/515
(58) Field of Classification Search ............... 548/515; 514/412
    See application file for complete search history.

(56) References Cited

U.S. PATENT DOCUMENTS

| | | | | |
|---|---|---|---|---|
| 2,490,714 | A | 12/1949 | Searle | 260/239 |
| 3,176,019 | A | 3/1965 | Campbell et al. | 260/293.4 |
| 5,001,160 | A | 3/1991 | McPherson et al. | 514/255 |
| 5,164,402 | A | 11/1992 | Brighty | 514/300 |
| 5,281,601 | A | 1/1994 | Cross et al. | 514/320 |
| 5,397,800 | A | 3/1995 | Alker et al. | 514/413 |
| 5,948,792 | A | 9/1999 | Tsuchiya et al. | 514/317 |
| 6,130,232 | A | 10/2000 | Mase et al. | 514/318 |
| 6,174,900 | B1 | 1/2001 | Okada et al. | 514/317 |
| 6,313,312 | B1 | 11/2001 | Banks et al. | 548/452 |

FOREIGN PATENT DOCUMENTS

| | | |
|---|---|---|
| CA | 2155320 | 8/1993 |
| EP | 0 325 571 | 7/1989 |
| EP | 0 388 054 | 9/1990 |
| EP | 0 413 455 | 2/1991 |
| EP | 0 613 232 | 8/1994 |
| EP | 0 801 067 | 10/1997 |
| EP | 0 823 423 | 2/1998 |
| EP | 0 863 141 | 9/1998 |
| GB | 940540 | 10/1963 |
| JP | 92921/1994 | 4/1994 |
| JP | 135958/1994 | 5/1994 |
| WO | WO 91/09013 | 6/1991 |
| WO | WO 93/16018 | 8/1993 |
| WO | WO 93/16048 | 8/1993 |
| WO | WO 96/33973 | 10/1996 |
| WO | WO 97/45414 | 12/1997 |
| WO | WO 98/05641 | 2/1998 |
| WO | WO 98/29402 | 7/1998 |
| WO | WO 98/53814 | 12/1998 |
| WO | WO 01/42212 | 6/2001 |
| WO | WO 01/42213 | 6/2001 |
| WO | WO 01/90081 | 11/2001 |
| WO | WO 02/00652 | 1/2002 |
| WO | WO 02/04402 | 1/2002 |
| WO | WO 02/06241 | 1/2002 |
| WO | WO 02/51841 | 7/2002 |
| WO | WO 02/053564 | 7/2002 |
| WO | WO 2004/004629 | 1/2004 |
| WO | WO 2004/005252 | 1/2004 |
| WO | WO 2004/014363 | 2/2004 |
| WO | WO 2004/014853 | 2/2004 |
| WO | WO 2004/018422 | 3/2004 |
| WO | WO 2004/052857 | 6/2004 |
| WO | WO 2004/056767 | 7/2004 |
| WO | WO 2004/056810 | 7/2004 |
| WO | WO 2004/056811 | 7/2004 |
| WO | WO 2004/089900 | 10/2004 |

OTHER PUBLICATIONS

Morissette et al. Advanced Drug Delivery Reviews 2004, 56, 275-300.*

(Continued)

*Primary Examiner*—Rebecca L Anderson
*Assistant Examiner*—Jason M Nolan
(74) *Attorney, Agent, or Firm*—Jayadeep R. Deshmukh, Esq.; George E. Heibel, Esq.

(57) ABSTRACT

This invention generally relates to the derivatives of novel 3,6 disubstituted azabicyclo[3.1.0]hexanes. The compounds of this invention are muscarinic receptor antagonists which are useful, inter-alia for the treatment of various diseases of the respiratory, urinary and gastrointestinal systems mediated through muscarinic receptors. The invention also relates to pharmaceutical compositions containing the compounds of the present invention and the methods of treating the diseases mediated through muscarinic receptors.

23 Claims, No Drawings

OTHER PUBLICATIONS

Wess et al. Life Sciences 2003, 72, 2047-2054.*
O'Neill, M. Drug Discovery Today Oct. 2005, 10(20), 1338.*
Michel et al. Naunyn-Schmiedeberg's Arch Pharmacol 2006, 374, 79-85.*
Latifpour et al. The Journal of Pharmacology and Experimental Therapeutics 1989, 249(1), 81-88.*
Carrier et al. The Journal of Pharmacology and Experimental Therapeutics 1987, 242(2), 531-535.*
Ahren et al. Diabetologia 1996, 39, 383-390.*
Abrams et al. British Journal of Pharmacology 2006, 148, 565-578.*
de Groat and Yoshimura, "Pharmacology of the Lower Urinary Tract", *Annual Review of Pharmacology and Toxicology*, 41:691-721 (2001).
Cheng and Prusoff, "Relationship between the inhibition constant ($K_1$) and the concentration of inhibitor which causes 50 per cent inhibition ($I_{50}$) of an enzymatic reaction", *Biochemical Pharmacology*, 22:3099-3108 (1973).
Birdsall et al., "Muscarinic receptors; it's a knockout", *Trends in Pharmacological Sciences*, 22(5):215-219 (2001).
Brighty et al., "Synthesis of (1α,5α,6α)-6-Amino-3-azabicyclo[3.1.0]hexane, a Novel Achiral Diamine", *Synlett*, 1097-1099 (1996).
Braish et al., "Construction of the (1α,5α,6α)-6-Amino-3-azabicyclo[3.1.0]hexane Ring System", *Synlett*, 1100-1102 (1996).
Chapple, "Muscarinic receptor antagonists in the treatment of overactive bladder", *Urology*, 55(Suppl. 5A):33-46 (2000).
Eglen et al., "Muscarinic receptor ligands and their theraputic potential", *Current Opinion in Chemical Biology*, 3:426-432 (1999).
Eglen et al., "Theraputic opportunities from muscarinic receptor research", *Trends in Pharmacological Sciences*, 22(8):409-414 (2001).
Felder et al., "Theraputic Opportunities for Muscarinic Receptors in the Central Nervous System", *Journal of Medicinal Chemistry*, 43(23):4333-4353 (2000).
Grover et al., "Chiral Mandelic Acid Template Provides a Highly Practical Solution for (S)-Oxybutynin Synthesis", *Journal of Organic Chemistry*, 65:6283-6287 (2000).
Shacklett and Smith, "The Preparation of Substituted Benzilic Acids", *Journal of the American Chemical Society*, 75:2654-2657 (1953).
Sagara et al., "Cyclohexylmethylpiperidinyltriphenylpropioamide: A Selective Muscarinic $M_3$ Antagonist Discriminating against the Other Receptor Subtypes", *Journal of Medicinal Chemistry*, 45:984-987 (2002).
Nkpa and Chedekel, "Mechanistic Studies on the Addition of Cysteine to 3,4-Dihydroxyphenylalanine", *Journal of Organic Chemistry*, 46:213-215 (1981).
Kadin and Cannon, "Esters of N-Methyl-3-hydroxypiperidine Having Psychotomimetic Activity. II", *Journal of Organic Chemistry*, 27:240-245 (1962).
Broadley and Kelly, "Muscarinic Receptor Agonists and Antagonists", *Molecules*, 6:142-193 (2001).
Moriya et al., "Affinity Profiles of Various Muscarinic Antagonists for Cloned Human Muscarinic Acetylcholine Receptor (mAChR) Subtypes and mAChRs in Rat Heart and Submandibular Gland", *Life Sciences*, 64(25):2351-2358 (1999).
Kubo et al., "Cloning, sequencing and expression of complementary DNA encoding the muscarinic acetylcholine receptor", *Nature*, 323(2):411-416 (1986).
Bonner et al., "Identification of a Family of Muscarinic Acetylcholine Receptor Genes", *Science*, 237:527-531 (1987).
Steers, "The future direction of neuro-urology drug research", *Current Opinion in CPNS Investigational Drugs*, 2(3):268-282.
Steers, Barrot, Wein, "Voiding dysfunction: diagnosis classification and management", In: *Adult and Pediatric Urology*, ed. Gillenwater, Grayhack, Howards, Duckett. Mosby, St. Louis, MO; 1220-1325, 3rd edition (1996).
Weinstock et al., "A General, One-Step Synthesis of α-keto Esters", *Synthetic Communications*, 11(12):943-946 (1981).
Vogel's textbook, "Practical Organic Chemistry" 1046-1047 (5th Ed.).
"Design of prodrugs", ed. H. Bundgaard, Elsevier (1985).

\* cited by examiner

3,6-DISUBSTITUTED AZABICYCLO [3.1.0] HEXANE DERIVATIVES USEFUL AS MUSCARINIC RECEPTOR ANTAGONISTS

FIELD OF THE INVENTION

This invention generally relates to the derivatives of novel 3,6-disubstituted azabicyclo[3.1.0]hexanes.

The compounds of this invention are muscarinic receptor antagonists which are useful, inter-alia, for the treatment of various diseases of the respiratory, urinary and gastrointestinal systems mediated through muscarinic receptors.

The invention also relates to pharmaceutical compositions containing the compounds of the present invention and the methods of treating the diseases mediated through muscarinic receptors.

BACKGROUND OF THE INVENTION

Muscarinic receptors as members of the G Protein Coupled Receptors (GPCRS) are composed of a family of 5 receptor sub-types ($M_1$, $M_2$, $M_3$, $M_4$ and $M_5$) and are activated by the neurotransmitter acetylcholine. These receptors are widely distributed on multiple organs and tissues and are critical to the maintenance of central and peripheral cholinergic neurotransmission. The regional distribution of these receptor sub-types in the brain and other organs has been documented. For example, the $M_1$ subtype is located primarily in neuronal tissues such as cereberal cortex and autonomic ganglia, the $M_2$ subtype is present mainly in the heart where it mediates cholinergically induced bradycardia, and the $M_3$ subtype is located predominantly on smooth muscle and salivary glands (*Nature*, 1986; 323: 411; Science, 1987; 237: 527).

A review in Current opinions in Chemical Biology, 1999; 3: 426, as well as in Trends in Pharmacological Sciences, 2001; 22: 409 by Eglen et. al., describe the biological potentials of modulating muscarinic receptor subtypes by ligands in different disease conditions like Alzheimer's disease, pain, urinary disease condition, chronic obstructive pulmonary disease etc.

A review in J. Med. Chem., 2000; 43: 4333 by Christian C. Felder et. al. describes therapeutic opportunities for muscarinic receptors in the central nervous system and elaborates on muscarinic receptor structure and function, pharmacology and their therapeutic uses.

The pharmacological and medical aspects of the muscarinic class of acetylcholine agonists and antagonists are presented in a review in Molecules, 2001, 6: 142.

N. J. M. Birdsall et. al. in Trends in Pharmacological Sciences, 2001; 22: 215 have also summarized the recent developments on the role of different muscarinic receptor subtypes using different muscaranic receptor of knock out mice.

Muscarinic agonists such as muscarine and pilocarpine and antagonists such as atropine have been known for over a century, but little progress has been made in the discovery of receptor subtype-selective compounds making it difficult to assign specific functions to the individual receptors. Although classical muscarinic antagonists such as atropine are potent bronchodilators, their clinical utility is limited due to high incidence of both peripheral and central adverse effects such as tachycardia, blurred vision, dryness of mouth, constipation, dementia, etc. Subsequent development of the quarterly derivatives of atropine such as ipratropium bromide are better tolerated than parenterally administered options but most of them are not ideal anti-cholinergic bronchodilators due to lack of selectivity for muscarinic receptor sub-types. The existing compounds offer limited therapeutic benefit due to their lack of selectivity resulting in dose limiting side-effects such as thirst, nausea, mydriasis and those associated with the heart such as tachycardia mediated by the $M_2$ receptor.

Annual review of Pharmacological Toxicol., 2001; 41: 691, describes the pharmacology of the lower urinary tract infections. Although anti muscarinic agents such as oxybutynin and tolterodine that act non-selectively on muscarinic receptors have been used for many years to treat bladder hyperactivity, the clinical effectiveness of these agents has been limited due to the side effects such as dry mouth, blurred vision and constipation. Tolterodine is considered to be generally better tolerated than oxybutynin. (W. D. Steers et. al. in Curr. Opin. Invest. Drugs, 2: 268, C. R. Chapple et. al. in Urology, 55: 33), Steers W D, Barrot D M, Wein A J, 1996, Voiding dysfunction: diagnosis classification and management. In Adult and Pediatric Urology, ed. J Y Gillenwatter, J T Grayhack, S S Howards, J W Duckett, pp 1220-1325, St. Louis, Mo.; Mosby. $3^{rd}$ edition.)

Despite these advances, there remains a need for development of new highly selective muscarinic antagonists which can interact with distinct subtypes, thus avoiding the occurrence of adverse effects.

Compounds having antagonistic activity against muscarinic receptors have been described in Japanese patent application Laid. Open Number 92921/1994 and 135958/1994; WO 93/16048; U.S. Pat. No. 3,176,019; GB 940,540; EP 0325 571; WO 98/29402; EP 0801067; EP 0388054; WO 9109013; U.S. Pat. No. 5,281,601. U.S. Pat. Nos. 6,174,900, 6,130,232 and 5,948,792; WO 97/45414 are related to 1,4-disubstituted piperidine derivatives; WO 98/05641 describes fluorinated, 1,4-disubstitued piperidine derivatives; WO 93/16018 and WO96/33973 are other close art references.

A report in J. Med. Chem., 2002; 44:984, describes cyclohexylmethyl piperidinyl triphenylpropioamide derivatives as selective $M_3$ antagonist discriminating against the other receptor subtypes.

SUMMARY OF THE INVENTION

The present invention provides novel 3,6-disubstituted azabicyclo[3.1.0]hexanes as muscarinic receptor antagonists which are useful as safe and effective therapeutic or prophylactic agents for the treatment of various diseases of the respiratory, urinary and gastrointestinal systems, and process for the synthesis of the novel compounds.

The invention also provides pharmaceutical compositions containing the novel compounds together with acceptable carriers, excipients or diluents which are useful for the treatment of various diseases of the respiratory, urinary and gastrointestinal systems.

The present invention also includes within its scope prodrugs of the novel compounds. In general, such prodrugs will be functionalized derivatives of these compounds which readily get converted in vivo into the defined compounds. Conventional procedures for the selection and preparation of suitable prodrugs are known to the artisan skilled in the art.

The invention also includes the enantiomers, diastereomers, N-oxides, polymorphs, pharmaceutically acceptable salts and pharmaceutically acceptable solvates of these compounds as well as metabolites having the same type of activity.

The invention further includes pharmaceutical compositions comprising the compounds of the present invention, their prodrugs, metabolites, enantiomers, diastereomers, N-oxides, polymorphs, solvates or pharmaceutically acceptable salts thereof, in combination with a pharmaceutically acceptable carrier and optionally included excipients.

Other advantages of the invention will be set forth in the description which follows, and in part will be apparent from the description or may be learnt by the practice of the invention. The objects and the advantages of the invention may be realized and obtained by means of the mechanisms and combinations pointed out in the appended claims.

In accordance with one aspect of the present invention, there is provided a compound having the structure of Formula I:

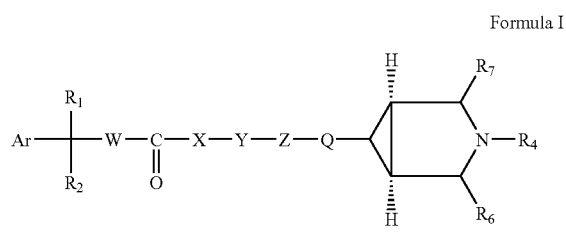

Formula I and its pharmaceutically acceptable salts, pharmaceutically acceptable solvates, esters, enantiomers, diastereomers, N-oxides, polymorphs, prodrugs, metabolites, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) amino or N-lower alkyl ($C_1$-$C_4$) amino carbonyl;

$R_1$ represents a hydrogen, hydroxy, hydroxy methyl, amino, alkoxy, carbamoyl or halogen (e.g. fluorine, chlorine, bromine and iodine);

$R_2$ represents aLkyl, $C_3$-$C_7$ cycloalkyl ring, a $C_3$-$C_7$ cyclo alkenyl ring, an aryl or a heteroaryl ring having 1 to 2 hetero atoms selected from a group consisting of oxygen, sulphur and nitrogen atoms; the aryl or a heteroaryl ring may be unsubstituted or substituted by one to three substituents independently selected from lower alkyl ($C_1$-$C_4$), lower perhalo alkyl ($C_1$-$C_4$), cyano, hydroxy, nitro, lower alkoxycarbonyl, halogen, lower alkoxy ($C_1$-$C_4$), lower perhalo alkoxy ($C_1$-$C_4$), unsubstituted amino, N-lower alkylamino ($C_1$-$C_4$), N-lower alkylamino carbonyl ($C_1$-$C_4$);

W represents $(CH_2)_p$, where p represents 0 to 1;

X represents an oxygen, sulphur, nitrogen or no atom;

Y represents $CHR_5CO$ wherein $R_5$ represents hydrogen or methyl or $(CH_2)q$ wherein q represents 0 to 4;

Z represents oxygen, sulphur, $NR_{10}$, wherein $R_{10}$ represents hydrogen, $C_{1-6}$ alkyl;

Q represents $(CH_2)_n$ wherein n represents 0 to 4, or $CHR_8$ wherein $R_8$ represents H, OH, $C_{1-6}$, alkyl, alkenyl alkoxy or $CH_2CHR_9$ wherein $R_9$ represents H, OH, lower alkyl ($C_1$-$C_4$) or lower alkoxy ($C_1$-$C_4$);

$R_6$ and $R_7$ are independently selected from COOH, H, $CH_3$, $CONH_2$, $NH_2$, $CH_2NH_2$;

$R_4$ represents $C_1$-$C_{15}$ saturated or unsaturated aliphatic hydrocarbon groups in which any 1 to 6 hydrogen atoms may be substituted with the group independently selected from halogen, arylalkyl, arylalkenyl, heteroarylalkyl or heteroarylalkenyl having 1 to 2 hetero atoms selected from a group consisting of nitrogen, oxygen and sulphur atoms with option that any 1 to 3 hydrogen atoms on the ring in said arylalkyl, arylalkenyl, hetero arylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$), N-lower alkylamino carbonyl ($C_1$-$C_4$).

In accordance with a second aspect of the present invention, there is provided a compound having the structure of Formula II (Formula I, when $R_6$ and $R_7$=H) and its pharmaceutically acceptable salts, pharmaceutically acceptable solvates, esters, enantiomers, diastereomers, N-oxides, polymorphs, prodrugs, metabolites, wherein Ar, $R_1$, $R_2$, W, X, Y, Z, Q, and $R_4$ are as defined for Formula I.

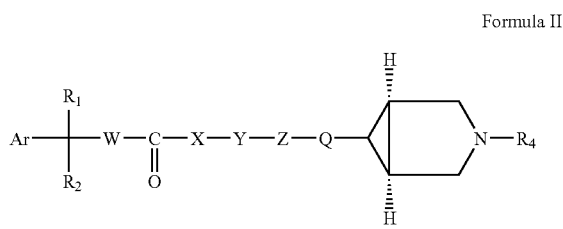

Formula II

In accordance with a third aspect of the present invention, there is provided a compound having the structure of Formula III (Formula I wherein W is $(CH_2)p$ where p=0, X is no atom and Y is $(CH_2)q$ where q=0, $R_6$=H, $R_7$=H) and its pharmaceutically acceptable salts, pharmaceutically acceptable solvates, esters, enantiomers, diastereomers, N-oxides, polymorphs, prodrugs, metabolites, wherein Ar, $R_1$, $R_2$, Z, Q and $R_4$ are as defined for Formula I.

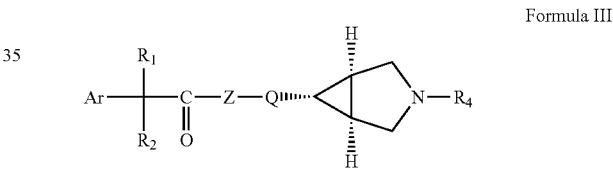

Formula III

In accordance with a fourth aspect of the present invention, there is provided a compound having the structure of Formula IV (Formula I wherein W is $(CH_2)p$ where p=0, X is no atom and Y is $(CH_2)q$ where q=0, $R_6$=H, $R_7$=H,

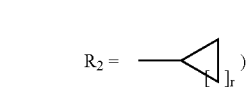

and its pharmaceutically acceptable salts, pharmaceutically acceptable solvates, esters, enantiomers, diastereomers, N-oxides, polymorphs, prodrugs, metabolites, wherein Ar, $R_1$, Z, Q and $R_4$ are as defined for Formula I and r is 1 to 4.

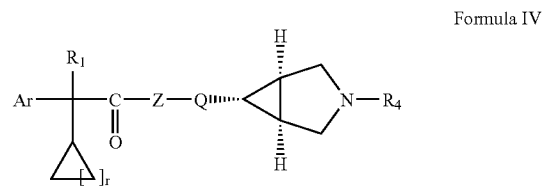

Formula IV

In accordance with a fifth aspect of the present invention, there is provided a compound having the structure of Formula V (Formula I wherein W is (CH$_2$)p where p=0, X is no atom and Y is (CH$_2$)q where q=0, R$_6$=H, R$_7$=H,

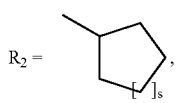

R$_1$ is hydroxy, Ar is phenyl), and its pharmaceutically acceptable salts, pharmaceutically acceptable solvates, esters, enantiomers, diastereomers, N-oxides, polymorphs, prodrugs, metabolites, wherein R$_4$, Z and Q are the same as defined for Formula I, s represents 1 to 2.

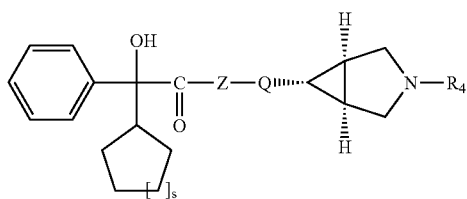

Formula V

In accordance with a sixth aspect of the present invention, there is provided a method for treatment or prophylaxis of an animal or a human suffering from a disease or disorder of the respiratory, urinary and gastrointestinal systems, wherein the disease or disorder is mediated through muscarinic receptors.

In accordance with a seventh aspect of the present invention, there is provided a method for treatment or prophylaxis of an animal or a human suffering from a disease or disorder associated with muscarinic receptors, comprising administering to a patient in need thereof, an effective amount for muscarinic receptor antagonist compound as described above.

In accordance with an eighth aspect of the present invention, there is provided a method for treatment or prophylaxis of an animal or a human suffering from a disease or disorder of the respiratory system such as bronchial asthma, chronic obstructive pulmonary disorders (COPD), pulmonary fibrosis, etc.; urinary system which induce such urinary disorders as urinary incontinence, lower urinary tract symptoms (LUTS), etc.; and gastrointestinal system such as irritable bowel syndrome, obesity, diabetes and gastrointestinal hyperkinesis with compounds as described above, wherein the disease or disorder is associated with muscarinic receptors.

In accordance with a ninth aspect of the present invention, there are provided processes for preparing the compounds as described above.

The compounds of the present invention are novel and exhibit significant potency in terms of their activity, which was determined by in vitro receptor binding and functional assays and in vivo experiments using anaesthetized rabbit. The compounds that were found active in in vitro assay were tested in vivo. Some of the compounds of the present invention were found to be potent muscarinic receptor antagonists with high affinity towards M$_3$ receptors. Therefore, the present invention provides the pharmaceutical compositions for the possible treatment for the disease or disorders associated with muscarinic receptors. In addition, the compounds of the present invention can be administered orally or parenterally.

DETAILED DESCRIPTION OF THE INVENTION

The compounds of the present invention may be prepared by techniques well known in the art and familiar to the average synthetic organic chemist. In addition, the compounds of the present invention may be prepared by the following novel and inventive reaction sequences:

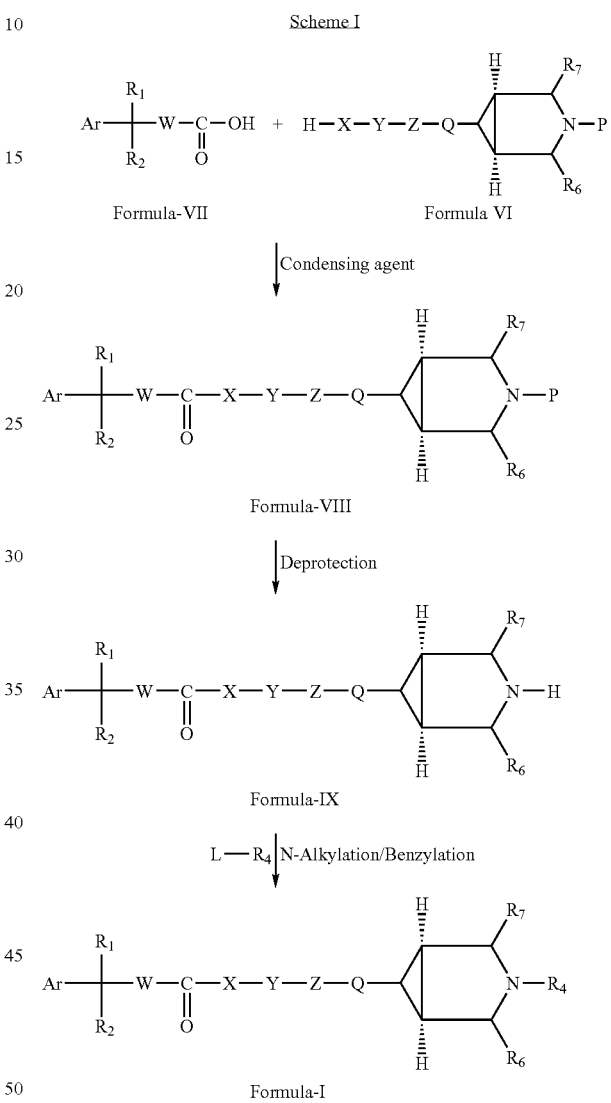

The compounds of Formula I of the present invention may be prepared by the reaction sequence as shown in Scheme I. The preparation comprises condensing a compound of Formula VII with the compound of Formula VI wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl (C$_1$-C$_4$), lower perhalo alkyl (C$_1$-C$_4$), cyano, hydroxy, nitro, lower alkoxy (C$_1$-C$_4$), lower perhalo alkoxy (C$_1$-C$_4$), unsubstituted amino, N-lower alkyl (C$_1$-C$_4$) amino or N-lower alkyl (C$_1$-C$_4$) amino carbonyl;

R$_1$ represents a hydrogen, hydroxy, hydroxy methyl, amino, alkoxy, carbamoyl or halogen (e.g. fluorine, chlorine, bromine and iodine);

$R_2$ represents alkyl, $C_3$-$C_7$ cycloalkyl ring, a $C_3$-$C_7$ cyclo alkenyl ring, an aryl or a heteroaryl ring having 1 to 2 hetero atoms selected from a group consisting of oxygen, sulphur and nitrogen atoms; the aryl or a heteroaryl ring may be unsubstituted or substituted by one to three substituents independently selected from lower alkyl ($C_1$-$C_4$), lower perhalo alkyl ($C_1$-$C_4$), cyano, hydroxy, nitro, lower alkoxycarbonyl, halogen, lower alkoxy ($C_1$-$C_4$), lower perhalo alkoxy ($C_1$-$C_4$), unsubstituted amino, N-lower alkylamino ($C_1$-$C_4$), N-lower alkylamino carbonyl ($C_1$-$C_4$);

W represents $(CH_2)_p$, where p represents 0 to 1;

X represents an oxygen, sulphur, nitrogen or no atom;

Y represents $CHR_5CO$ wherein $R_5$ represents hydrogen or methyl or $(CH_2)q$ wherein q represents 0 to 4;

Z represents oxygen, sulphur, $NR_{10}$, wherein $R_{10}$ represents hydrogen, $C_{1-6}$alkyl;

Q represents $(CH_2)_n$ wherein n represents 0 to 4, or $CHR_8$ wherein $R_8$ represents H, OH, $C_{1-6}$, alkyl, alkenyl alkoxy or $CH_2CHR_9$ wherein $R_9$ represents H, OH, lower alkyl ($C_1$-$C_4$) or lower alkoxy ($C_1$-$C_4$);

$R_6$ and $R_7$ are independently selected from COOH, H, $CH_3$, $CONH_2$, $NH_2$, $CH_2NH_2$;

P is any protecting group for an amino group, in the presence of a condensing agent to give a protected compound of Formula VIII which on deprotection in the presence of a deprotecting agent in an organic solvent gives an unprotected intermediate of Formula IX which is finally N-alkylated or benzylated with a suitable alkylating or benzylating agent L-$R_4$ to give a compound of Formula I wherein L is any leaving group and $R_4$ is as defined above.

P is any protecting group for an amino group for a compound of Formula VI and is selected from benzyl and t-butyloxy carbonyl groups.

The reaction of the compound of Formula VII with a compound of Formula VI to give a compound of Formula VIII is carried out in the presence of a condensing agent which is selected from the group consisting of 1-(3-dimethylaminopropyl)-3-ethyl carbodiimide hydrochloride (EDC) and 1,8-diazabicyclo[5.4.0]undec-7-ene (DBU).

The reaction of the compound of Formula VII with a compound of Formula VI to give a compound of Formula VIII is carried out in a suitable solvent selected from the group consisting of N,N-dimethylformamide, dimethylsulfoxide, toluene, and xylene at a temperature ranging from about 0-140° C.

The deprotection of the compound of Formula VIII to give a compound of Formula IX is carried out with a deprotecting agent which is selected from the group consisting of palladium on carbon, trifluoroacetic acid (TFA) and hydrochloric acid.

The deprotection of the compound of Formula VIII to give a compound of Formula IX is carried out in a suitable organic solvent selected from the group consisting of methanol, ethanol, tetrahydrofuran and acetonitrile at temperatures ranging from about 10-50° C.

The N-alkylation or benzylation of the compound of Formula IX to give a compound of Formula I is carried out with a suitable alkylating or benzylating agent, L-$R_4$ wherein L is any leaving group, known in the art, preferably selected from halogen, O-mestyl and O-tosyl group.

The N-alkylation or benzylation of the compound of Formula IX to give a compound of Formula I is carried out in a suitable organic solvent such as N,N-dimethylformamide, dimethyl sulfoxide, tetrahydrofuran and acetonitrile, at temperatures ranging from about 25-100° C.

In the above scheme, where specific bases, condensing agents, protecting groups, deprotecting agents, N-alkylating/benzylating agents, solvents, catalysts etc. are mentioned, it is to be understood that other bases, condensing agents, protecting groups, deprotecting agents, N-alkylating/benzylating agents, solvents, catalysts etc. known to those skilled in the art may be used. Similarly, the reaction temperature and duration may be adjusted according to the desired needs.

Alternatively, the compounds of the invention may be prepared by condensing compounds of formula VI with an aryl alpha keto ester (Ar(CO)COOR' wherin R' denotes a lower alkyl group) and the compounds thus formed may be subsequently reacted with the condensate R"M, wherein R" groups include groups such as phenyl, C4-6 alkyl etc. and M may be alkali metal or MgX, wherein x is a halogen atom. Alpha keto esters may in turn be prepared by following J.O.C., 46, 213 (1981), or synthetic communication, 11, 943(1981).

The compounds of the invention may also be prepared by reacting R"M (wherein M and R" have the same as described above) with the aryl alpha keto ester (Ar(CO)COOR' wherin R' denotes a lower alkyl group) to form an alpha hydroxy ester. This product is further reacted with compound of formula VI and then the protecting group is removed to give compounds of formula VIII.

Suitable salts of the compounds represented by the Formula I were prepared so as to solubilize the compound in aqueous medium for biological evaluations. Examples of such salts include pharmacologically acceptable salts such as inorganic acid salts (e.g. hydrochloride, hydrobromide, sulphate, nitrate and phosphorate), organic acid salts(e.g. acetate, tartarate, citrate, fumarate, maleate, tolounesulphonate and methanesulphonate). When carboxyl group is included in the Formula I as a substituent, it may be an alkali metal salt(e.g. sodium, potassium, calcium, magnesium, and the like). These salts may be prepared by the usual prior art techniques, such as treating the compound with an equivalent amount of inorganic or organic, acid or base in a suitable solvent.

Preferred compounds according to the invention and capable of being produced by Scheme I as shown in Table-I include:

| Compound No. | Chemical Name |
|---|---|
| 1. | (1α,5α,6α)-N-[3-benzyl-3-azabicyclo[3.1.0]hexyl-6-(aminomethyl)-yl]-2-hydroxy-2,2-diphenyl acetamide |
| 2. | (1α,5α,6α)-N-[3-benzyl-3-azabicyclo[3.1.0]hexyl-6-(aminomethyl)-yl]-2-hydroxy-2-cyclohexyl-2-phenyl acetamide |
| 3. | (1α,5α,6α)-N-[3-benzyl-3-azabicyclo[3.1.0]hexyl-6-(aminomethyl)-yl]-2-hydroxy-2-cyclopentyl-2-phenyl acetamide |
| 4. | (1α,5α,6α)-[3-benzyl-3-azabicyclo[3.1.0]hexyl-6-(methyl)-yl]-2-hydroxy-2,2-diphenyl acetate |
| 5. | (1α,5α,6α)-[3-benzyl-3-azabicyclo[3.1.0]hexyl-6-(methyl)-yl]-2-hydroxy-2-cyclohexyl-2-phenyl acetate |
| 6. | (1α,5α,6α)-[3-benzyl-3-azabicyclo[3.1.0]hexyl-6-(methyl)-yl]-2-hydroxy-2-cyclopentyl-2-phenyl acetate |
| 7. | (1α,5α,6α)-[3-(2-(2,3-dihydrobenzofuran-5-yl)ethyl)-3-azabicyclo[3.1.0]hexyl-6-(methyl)-yl]-2-hydroxy-2-cyclohexyl-2-phenyl acetate |
| 8. | (1α,5α,6α)-[3-(2-(2,3-dihydrobenzofuran-5-yl)ethyl)-3-azabicyclo[3.1.0]hexyl-6-(methyl)-yl]-2-hydroxy-2-cyclopentyl-2-phenyl acetate |
| 9. | (1α,5α,6α)-N-[3-(2-(2,3-dihydrobenzofuran-5-yl)ethyl)-3-azabicyclo[3.1.0]hexyl-6-(aminomethyl)-yl]-2-hydroxy-2-cyclohexyl-2-phenyl acetamide |
| 10. | (1α,5α,6α)-N-[3-(2-(2,3-dihydrobenzofuran-5-yl)ethyl)-3-azabicyclo[3.1.0]hexyl-6-(aminomethyl)-yl]-2-hydroxy-2-cyclopentyl-2-phenyl acetamide |

-continued

| Compound No. | Chemical Name |
|---|---|
| 11. | (1α,5α,6α)-[3-(2-(3,4-methylenedioxyphenyl)ethyl)-3-azabicyclo[3.1.0]hexyl-6-(methyl)-yl]-2-hydroxy-2-cyclopentyl-2-phenyl acetate |
| 12. | (1α,5α,6α)-[3-(2-(3,4-methylenedioxyphenyl)ethyl)-3-azabicyclo[3.1.0]hexyl-6-(methyl)-yl]-2-hydroxy-2-cyclohexyl-2-phenyl acetate |
| 13. | (1α,5α,6α)-N-[3-(2-(3,4-methylenedioxyphenyl)ethyl)-3-azabicyclo[3.1.0]hexyl-6-(aminomethyl)-yl]-2-hydroxy-2-cyclopentyl-2-phenyl acetamide |
| 14. | (1α,5α,6α)-N-[3-(2-(3,4-methylenedioxyphenyl)ethyl)-3-azabicyclo[3.1.0]hexyl-6-(aminomethyl)-yl]-2-hydroxy-2-cyclohexyl-2-phenyl acetamide |
| 15. | (1α,5α,6α)-N-[3-(4-methyl-3-pentenyl)-3-azabicyclo[3.1.0]hexyl-6-(aminomethyl)-yl]-2-hydroxy-2-cyclohexyl-2-phenyl acetamide |
| 16. | (1α,5α,6α)-N-[3-(4-methyl-3-pentenyl)-3-azabicyclo[3.1.0]hexyl-6-(aminomethyl)-yl]-2-hydroxy-2-cyclopentyl-2-phenyl acetamide |
| 17. | (1α,5α,6α)-[3-(4-methyl-3-pentenyl)-3-azabicyclo[3.1.0]hexyl-6-(methyl)-yl]-2-hydroxy-2-cyclopentyl-2-phenyl acetate |
| 18. | (1α,5α,6α)-[3-(4-methyl-3-pentenyl)-3-azabicyclo[3.1.0]hexyl-6-(methyl)-yl]-2-hydroxy-2-cyclopentyl-2-phenyl acetate |
| 19. | (1α,5α,6α)-[3-(1-phenylethyl)-3-azabicyclo[3.1.0]hexyl-6-(methyl)-yl]-2-hydroxy-2-cyclopentyl-2-phenyl acetate |
| 20. | (1α,5α,6α)-[3-(1-phenylethyl)-3-azabicyclo[3.1.0]hexyl-6-(methyl)-yl]-2-hydroxy-2-cyclohexyl-2-phenyl acetate |
| 21. | (1α,5α,6α)-N-[3-(1-phenylethyl)-3-azabicyclo[3.1.0]hexyl-6-(aminomethyl)-yl]-2-hydroxy-2-cyclohexyl-2-phenyl acetamide |
| 22. | (1α,5α,6α)-N-[3-(1-phenylethyl)-3-azabicyclo[3.1.0]hexyl-6-(aminomethyl)-yl]-2-hydroxy-2-cyclopentyl-2-phenyl acetamide |
| 23. | (1α,5α,6α)-N-[3-benzyl-3-azabicyclo[3.1.0]hexyl-6-(1-aminoethyl)-yl]-2-hydroxy-2,2-diphenyl acetamide |
| 24. | (1α,5α,6α)-N-[3-benzyl-3-azabicyclo[3.1.0]hexyl-6-(1-aminoethyl)-yl]-2-hydroxy-2-cyclohexyl-2-phenyl acetamide |
| 25. | (1α,5α,6α)-N-[3-benzyl-3-azabicyclo[3.1.0]hexyl-6-(1-aminoethyl)-yl]-2-hydroxy-2-cyclopentyl-2-phenyl acetamide |
| 26. | (1α,5α,6α)-[3-(3-methyl-2-butenyl)-3-azabicyclo[3.1.0]hexyl-6-(methyl)-yl]-2-hydroxy-2-cyclohexyl-2-phenyl acetate |
| 27. | (1α,5α,6α)-[3-(3-methyl-2-butenyl)-3-azabicyclo[3.1.0]hexyl-6-(methyl)-yl]-2-hydroxy-2-cyclopentyl-2-phenyl acetate |
| 28. | (2R)-(+)-(1α,5α,6α)-N-[3-benzyl-3-azabicyclo[3.1.0]hexyl-6-(aminomethyl)-yl]-2-hydroxy-2-cyclohexyl-2-phenyl acetamide |
| 29. | (2R)-(+)-(1α,5α,6α)-N-[3-benzyl-3-azabicyclo[3.1.0]hexyl-6-(aminomethyl)-yl]-2-hydroxy-2-cyclopentyl-2-phenyl acetamide |
| 30. | (2R)(+)-(1α,5α,6α)-[3-benzyl-3-azabicyclo[3.1.0]hexyl-6-(methyl)-yl]-2-hydroxy-2-cyclohexyl-2-phenyl acetate |
| 31. | (2R)(+)-(1α,5α,6α)-[3-benzyl-3-azabicyclo[3.1.0]hexyl-6-(methyl)-yl]-2-hydroxy-2-cyclopentyl-2-phenyl acetate |
| 32. | (2S)-(−)-(1α,5α,6α)-N-[3-benzyl-3-azabicyclo[3.1.0]hexyl-6-(aminomethyl)-yl]-2-hydroxy-2-cyclopentyl-2-phenyl acetamide |
| 33. | (2S)-(−)-(1α,5α,6α)-[3-benzyl-3-azabicyclo[3.1.0]hexyl-6-(methyl)-yl]-2-hydroxy-2-cyclopentyl-2-phenyl acetate |
| 34. | (1α,5α,6α)-N-[3-benzyl-3-azabicyclo[3.1.0]hexyl-6-(methyl)-yl]-2-hydroxy-2-cyclopentyl-2-phenyl acetamide L-(+)-tartrate salt |
| 35. | (2S)-(−)-(1α,5α,6α)-N-[3-benzyl-3-azabicyclo[3.1.0]hexyl-6-(aminomethyl)-yl]-2-hydroxy-2-cyclopentyl-2-phenyl acetamine. L-(+)-tartrate salt |
| 36. | (2R)-(+)-(1α,5α,6α)-N-[3-benzyl-3-azabicyclo[3.1.0]hexyl-6-(aminomethyl)-yl]-2-hydroxy-2-cyclopentyl-2-phenyl acetamide. L-(+)-tartrate salt |
| 37. | (1α,5α,6α)-N-[3-benzyl-3-azabicyclo[3.1.0]hexyl-6-(aminomethyl)-yl]-2-hydroxy-2-cyclobutyl-2-phenyl acetamide |
| 38. | (1α,5α,6α)-N-[3-benzyl-3-azabicyclo[3.1.0]hexyl-6-(aminomethyl)-yl]-2-hydroxy-2-cyclopropyl-2-phenyl acetamide |
| 39. | (1α,5α,6α)-N-[3-(3-methyl-2-butenyl)-3-azabicyclo[3.1.0]hexyl-6-(aminomethyl)-yl]-2-hydroxy-2-hexyl-2-phenyl acetamide |
| 40. | (1α,5α,6α)-[3-(3,4-methylenedioxyphenyl)methyl-3-azabicyclo[3.1.0]hexyl-6-(methyl)-yl]-2-hydroxy-2-cyclopentyl-2-phenyl acetate |
| 41. | (1α,5α,6α)-[3-(2-(3,4-methylenedioxyphenyl)ethyl)-3-azabicyclo[3.1.0]hexyl-6-(methyl)-yl]-2-hydroxy-2-cyclopentyl-2-phenyl acetate. L-(+)-tartrate salt |
| 42. | (1α,5α,6α)-[3-benzyl-3-azabicyclo[3.1.0]hexyl-6-(methyl)-yl]-2-hydroxy-2,2 diphenyl acetate L(+)-tartrate salt |
| 43. | (1α,5α,6α)-[3-benzyl-3-azabicyclo[3.1.0]hexyl-6-(methyl)-yl]-2-hydroxy-2-cyclohexyl-2-phenyl acetate L(+)-tartrate salt |
| 44. | (1α,5α,6α)-[3-benzyl-3-azabicyclo[3.1.0]hexyl-6-(methyl)-yl]-2-hydroxy-2-cyclopentyl-2-phenyl acetate L(+)-tartrate salt. |
| 45. | (1α,5α,6α)-N-[3-(3-pyridylmethyl)-3-azabicyclo[3.1.0]hexyl-6-(aminomethyl)-yl]-2-hydroxy-2-cyclohexyl-2-phenyl acetamide |
| 46. | (1α,5α,6α)-N-[3-(4-pyridylmethyl)-3-azabicyclo[3.1.0]hexyl-6-(aminomethyl)-yl]-2-hydroxy-2-cyclohexyl-2-phenyl acetatamide |
| 47. | (1α,5α,6α)-N-[3-(2-pyridylmethyl)-3-azabicyclo[3.1.0]hexyl-6-(aminomethyl)-yl]-2-hydroxy-2-cyclopentyl-2-phenyl acetamide |
| 48. | (1α,5α,6α)-N-[3-(4-pyridylmethyl)-3-azabicyclo[3.1.0]hexyl-6-(aminomethyl)-yl]-2-hydroxy-2-cyclopentyl-2-phenyl acetamide |
| 49. | (1α,5α,6α)-N-[3-(3-pyridylmethyl)-3-azabicyclo[3.1.0]hexyl-6-(aminomethyl)-yl]-2-hydroxy-2,2-diphenyl acetamide |
| 50. | (1α,5α,6α)-N-[3-(4-pyridylmethyl)-3-azabicyclo[3.1.0]hexyl-6-(aminomethyl)-yl]-2-hydroxy-2,2-diphenyl acetamide |
| 51. | (1α,5α,6α)-N-[3-(2-pyridylmethyl)-3-azabicyclo[3.1.0]hexyl-6-(aminomethyl)-yl]-2-hydroxy-2,2-diphenyl acetamide |
| 52. | (1α,5α,6α)-N-[3-(2-pyridylmethyl)-3-azabicyclo[3.1.0]hexyl-6-(aminomethyl)-yl]-2-hydroxy-2-cyclopentyl-2-phenyl acetamide |
| 53. | (1α,5α,6α)-N-[3-(3-pyridylmethyl)-3-azabicyclo[3.1.0]hexyl-6-(aminomethyl)-yl]-2-hydroxy-2-cyclopentyl-2-phenyl acetamide |
| 54. | (1α,5α,6α)-N-[3-(3-methyl-2-butenyl)-3-azabicyclo[3.1.0]hexyl-6-(aminomethyl)-yl]-2-hydroxy-2-cyclopentyl-2-phenyl acetamide |
| 55. | (1α,5α,6α)-N-[3-(3,4-methylenedioxyphenyl)methyl-3-azabicyclo[3.1.0]hexyl-6-(aminomethyl)-yl]-2-hydroxy-2-cyclopentyl-2-phenyl acetamide |
| 56. | (1α,5α,6α)-N-[3-(3,4-methylenedioxyphenyl)methyl-3-azabicyclo[3.1.0]hexyl-6-(aminomethyl)-yl]-2-hydroxy-2-cyclohexyl-2-phenyl acetamide |
| 57. | (1α,5α,6α)-[3-(4-methyl-3-pentenyl)-3-azabicyclo[3.1.0]hexyl-6-(methyl)-yl]-2-hydroxy-2-cyclohexyl-2-phenyl acetate-L-(+) tartrate salt |
| 58. | (1α,5α,6α)-[3-(2-(3,4-methylenedioxyphenyl)ethyl)-3-azabicyclo[3.1.0]hexyl-6-(methyl)-yl]-2-hydroxy-2-cyclohexyl-2-phenyl acetate. L-(+) tartrate salt |
| 59. | (1α,5α,6α)-[3-(1-phenylethyl)-3-azabicyclo[3.1.0]hexyl-6-(methyl)-yl]-2-hydroxy-2-cyclopentyl-2-phenyl acetate. L-(+) tartrate salt |
| 60. | (1α,5α,6α)-N-[3-benzyl-3-azabicyclo [3.1.0]-hexyl-6-(aminomethyl)-yl]-2-hydroxy-2-cyclopentyl-2-phenyl acetamide hydrochloride salt |
| 61. | (1α,5α,6α)-N-[3-benzyl-3-azabicyclo [3.1.0]-hexyl-6-(aminomethyl)-yl]-2-hydroxy-2-cyclopentyl-2-phenyl acetamide L-(−) malic acid salt |
| 62. | (1α,5α,6α)-N-[3-benzyl-3-azabicyclo [3.1.0]-hexyl-6-(aminomethyl)-yl]-2-hydroxy-2-cyclopentyl-2-phenyl acetamide maleate salt |

TABLE I

Formula III

Ar—C(R₁)(R₂)—C(=O)—Z—Q—[3-azabicyclo[3.1.0]hexane]—N—R₄

(Formula I, wherein W = (CH₂)p where p = 0, X is no atom and Y = (CH₂)q, where q = 0, R₆ = R₇ = H)

| Compound No. | Ar | R₁ | R₂ | Z | Q | R₄ |
|---|---|---|---|---|---|---|
| 1. | phenyl | OH | phenyl | NH | CH₂ | benzyl (phenethyl) |
| 2. | phenyl | OH | cyclohexyl | NH | CH₂ | phenethyl |
| 3. | phenyl | OH | cyclopentyl | NH | CH₂ | phenethyl |
| 4. | phenyl | OH | phenyl | O | CH₂ | phenethyl |
| 5. | phenyl | OH | cyclohexyl | O | CH₂ | phenethyl |
| 6. | phenyl | OH | cyclopentyl | O | CH₂ | phenethyl |
| 7. | phenyl | OH | cyclohexyl | O | CH₂ | 2,3-dihydrobenzofuran-5-yl-propyl |
| 8. | phenyl | OH | cyclopentyl | O | CH₂ | 2,3-dihydrobenzofuran-5-yl-propyl |
| 9. | phenyl | OH | cyclohexyl | NH | CH₂ | 2,3-dihydrobenzofuran-5-yl-propyl |
| 10. | phenyl | OH | cyclopentyl | NH | CH₂ | 2,3-dihydrobenzofuran-5-yl-propyl |
| 11. | phenyl | OH | cyclopentyl | O | CH₂ | 2,3-dihydrobenzofuran-5-yl-propyl |

TABLE I-continued

Formula III (Formula I, wherein W = (CH₂)p where p = 0, X is no atom and Y = (CH₂)q, where q = 0, R₆ = R₇ = H)

| Compound No. | Ar | R₁ | R₂ | Z | Q | R₄ |
|---|---|---|---|---|---|---|
| 12. | phenyl | OH | cyclohexyl | O | CH₂ | 2,3-dihydrobenzofuran-5-yl propyl |
| 13. | phenyl | OH | cyclopentyl | NH | CH₂ | 2,3-dihydrobenzofuran-5-yl propyl |
| 14. | phenyl | OH | cyclohexyl | NH | CH₂ | 2,3-dihydrobenzofuran-5-yl propyl |
| 15. | phenyl | OH | cyclohexyl | NH | CH₂ | 2-methyl-2-pentenyl |
| 16. | phenyl | OH | cyclopentyl | NH | CH₂ | 2-methyl-2-pentenyl |
| 17. | phenyl | OH | cyclohexyl | O | CH₂ | 2-methyl-2-pentenyl |
| 18. | phenyl | OH | cyclopentyl | O | CH₂ | 2-methyl-2-pentenyl |
| 19. | phenyl | OH | cyclopentyl | O | CH₂ | 1-phenylethyl |
| 20. | phenyl | OH | cyclohexyl | O | CH₂ | 1-phenylethyl |
| 21. | phenyl | OH | cyclohexyl | NH | CH₂ | 1-phenylethyl |
| 22. | phenyl | OH | cyclopentyl | NH | CH₂ | 1-phenylethyl |

TABLE I-continued

Formula III

[Structure of Formula III: Ar—C(R₁)(R₂)—C(=O)—Z—Q—(cyclopropane-fused pyrrolidine)—N—R₄]

(Formula I, wherein W = (CH₂)p where p = 0, X is no atom and Y = (CH₂)q, where q = 0, $R_6$ = $R_7$ = H)

| Compound No. | Ar | R₁ | R₂ | Z | Q | R₄ |
|---|---|---|---|---|---|---|
| 23. | phenyl | OH | phenyl | NH | CHCH₃ | benzyl |
| 24. | phenyl | OH | cyclohexyl | NH | CHCH₃ | benzyl |
| 25. | phenyl | OH | cyclopentyl | NH | CHCH₃ | benzyl |
| 26. | phenyl | OH | cyclohexyl | O | CH₂ | 3-methyl-2-butenyl |
| 27. | phenyl | OH | cyclopentyl | O | CH₂ | 3-methyl-2-butenyl |
| 28. | phenyl | OH | cyclohexyl | NH | CH₂ | benzyl |
| 29. | phenyl | OH | cyclopentyl | NH | CH₂ | benzyl |
| 30. | phenyl | OH | cyclohexyl | O | CH₂ | benzyl |
| 31. | phenyl | OH | cyclopentyl | O | CH₂ | benzyl |
| 32. | phenyl | OH | cyclopentyl | NH | CH₂ | benzyl |
| 33. | phenyl | OH | cyclopentyl | O | CH₂ | benzyl |
| 34 | L-(+) Tartaric acid salt of compound shown in Compound Number 3 in this table | | | | | |
| 35 | L-(+) Tartaric acid salt of compound shown in Compound Number 32 in | | | | | |

TABLE I-continued

Formula III (Formula I, wherein W = (CH$_2$)p where p = 0, X is no atom and Y = (CH$_2$)q, where q = 0, R$_6$ = R$_7$ = H)

| Compound No. | Ar | R$_1$ | R$_2$ | Z | Q | R$_4$ |
|---|---|---|---|---|---|---|
| 36 | L-(+) Tartaric acid salt of compound shown in Compound Number 29 in this table | | | | | |
| 37 | phenyl | OH | cyclobutyl | NH | CH$_2$ | phenethyl |
| 38 | phenyl | OH | cyclopropyl | NH | CH$_2$ | phenethyl |
| 39 | phenyl | OH | cyclohexyl | NH | CH$_2$ | 3-methyl-2-butenyl |
| 40 | phenyl | OH | cyclopentyl | O | CH$_2$ | benzo[1,3]dioxol-5-ylethyl |
| 41 | L (+)-Tartrate salt of compound shown in Compound Number 11 of this table | | | | | |
| 42 | L (+)-Tartrate salt of compound shown in Compound Number 4 of this table | | | | | |
| 43 | L (+)-Tartrate salt of compound shown in Compound Number 5 of this table | | | | | |
| 44 | L (+)-Tartrate salt of compound shown in Compound Number 6 of this table | | | | | |
| 45 | phenyl | OH | cyclohexyl | NH | CH$_2$ | 3-pyridylethyl |
| 46 | phenyl | OH | cyclohexyl | NH | CH$_2$ | 4-pyridylethyl |
| 47 | phenyl | OH | cyclohexyl | NH | CH$_2$ | 2-pyridylethyl |

TABLE I-continued
Formula III
(Formula I, wherein W = (CH₂)p where p = 0, X is no atom and Y = (CH₂)q, where q = 0, R₆ = R₇ = H)
| Compound No. | Ar | R₁ | R₂ | Z | Q | R₄ |
|---|---|---|---|---|---|---|
| 48 | 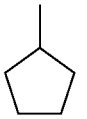 | OH | 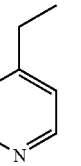 | NH | CH₂ |  |
| 49 | 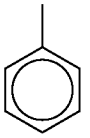 | OH | 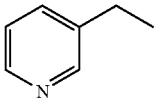 | NH | CH₂ |  |
| 50 |  | OH | 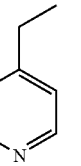 | NH | CH₂ |  |
| 51 | 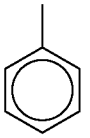 | OH | 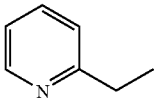 | NH | CH₂ |  |
| 52 | 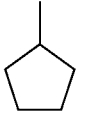 | OH | 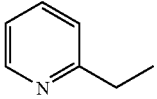 | NH | CH₂ |  |
| 53 | 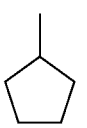 | OH | 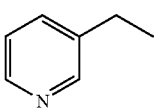 | NH | CH₂ |  |
| 54 | 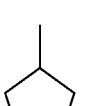 | OH |  | NH | CH₂ |  |
| 55 | 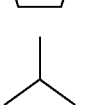 | OH |  | NH | CH₂ |  |
| 56 | 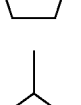 | OH | 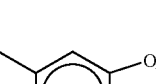 | NH | CH₂ | |

TABLE I-continued

Formula III

Ar—C(R₁)(R₂)—Z—Q·····[cyclopropane-fused pyrrolidine]—N—R₄

(Formula I, wherein W = (CH₂)p where p = 0, X is no atom and
Y = (CH₂)q, where q = 0, R₆ = R₇ = H)

| Compound No. | Ar | R₁ | R₂ | Z | Q | R₄ |
|---|---|---|---|---|---|---|
| 57 | | | L-(+) Tartaric salt of compound 17 | | | |
| 58 | | | L-(+) Tartaric salt of compound 12 | | | |
| 59 | | | L-(+) Tartrate salt of compound No. 19 | | | |
| 60 | | | Hydrochloride salt of compound No. 3 | | | |
| 61 | | | L-(−) Malic acid salt of compound No. 3 | | | |
| 62 | | | Maleate salt of compound No. 3 | | | |

Because of their valuable pharmacological properties, the compounds of the present invention may be administered to an animal for treatment orally, or by parenteral route. The pharmaceutical compositions of the present invention are preferably produced and administered in dosage units, each unit containing a certain amount of at least one compound of the invention and/or at least one physiologically acceptable addition salt thereof. The dosage may be varied over extremely wide limits as the compounds are effective at low dosage levels and relatively free of toxicity. The compounds may be administered in the low micromolar concentration, which is therapeutically effective, and the dosage may be increased as desired up to the maximum dosage tolerated by the patient.

The present invention also includes within its scope prodrugs of the compounds of Formulae I, II, III, IV and V. In general, such prodrugs will be functional derivatives of these compounds, which readily are converted in vivo into the defined compounds. Conventional procedures for the selection and preparation of suitable prodrugs are known.

The present invention also includes the enantiomers, diastereomers, N-Oxides, polymorphs, solvates and pharmaceutically acceptable salts of these compounds as well as metabolites having the same type of activity. The present invention further includes pharmaceutical composition comprising the molecules of Formulae I, II, III, IV and V or prodrugs, metabolites, enantiomers, diastereomers, N-oxides, polymorphs, solvates or pharmaceutically acceptable salts thereof, in combination with pharmaceutically acceptable carrier and optionally included excipient.

The examples mentioned below demonstrate the general synthetic procedure as well as the specific preparation of the preferred compound. The examples are provided to illustrate the details of the invention and should not be constrained to limit the scope of the present invention.

Experimental Details

Various solvents, such as acetone, methanol, pyridine, ether, tetrahydrofuran, hexanes, and dichloromethane, were dried using various drying reagents according to the procedure described in the literature. IR spectra were recorded as nujol mulls or a thin neat film on a Perkin Elmer Paragon instrument, Nuclear Magnetic Resonance (NMR) were recorded on a Varian XL-300 MHz instrument using tetramethylsilane as an internal standard.

EXAMPLE 1

Preparation of (1α,5α,6α)-N-[3-benzyl-3-azabicyclo [3.1.0]hexyl-6-(aminomethyl)-yl]-2-hydroxy-2,2-diphenyl acetamide (Compound No. 1)

Step a: Preparation of 2-hydroxy-2,2-diphenyl acetic acid

Synthesized as per reported procedures in Vogel's textbook of practical organic chemistry page 1046 (5$^{th}$ Ed); *J. Am. Chem. Soc.*, 75, 2654(1953) and EP 613232.

Step b: Preparation of (1α,5α,6α)-6-aminomethyl-3-benzyl-3-azabicyclo[3.1.0]hexane Synthesized as per reported procedures described in EP 0 413 455; U.S. Pat. No. 2,490,714 and Synlett, 1097-1102 (1996).

Step c: To a solution of (1α,5α,6α)-6-aminomethyl-3-benzyl-3-azabicyclo[3.1.0]hexane (1 mmol, 0.202 gm) in dimethyl formamide, DMF (5 ml) was added 2-hydroxy-2,2-diphenyl acetic acid (1 mmol, 0.225 gm) and cooled to 0° C. The reaction mixture was treated with hydroxy benzotriazole (1 mmol, 0.135 g) followed by N-methyl morpholine (2 mmol, 0.202 gm) and stirred at 0° C. for 0.5 hrs. EDC (1-[3-(dimethylamino)propyl]-3-ethyl carbodiimide hydrochloride (1 mmol, 0.192 gms) was added and the reaction mixture (RM) was stirred at 0° C. for 1 hour and at room temperature (RT) overnight. The RM was then poured into cold water and extracted with ethyl acetate. The combined organic layers were washed with water and dried over sodium sulphate. The crude compound obtained after removing the solvent was purified by column chromatography (silicagel 100-200 mesh), eluting the compound with 30-70 ethyl acetate-hexane mixture.

$^1$H-NMR (CDCl$_3$) δ—values:7.47-7.17 (m, arom, 15H), 3.58 (s, 2H, benzylic), 3.18-3.14 (t, 2H), 2.95-2.92 (d, 2H), 2.35-2.32 (m, 2H ), 2.04 (s, 1H) 1.28-1.23 (m, 1H), 0.94-0.91 (m, 2H)

IR (DCM): 1658 cm$^{-1}$ (amide carbonyl)

EXAMPLE 2

Preparation of (1α,5α,6α)-N-[3-benzyl-3-azabicyclo [3.1.0]hexyl-6-(aminomethyl)-yl]-2-hydroxy-2-cyclohexyl-2-phenyl acetamide (Compound No. 2)

Step a: Preparation of 2-hydroxy-2-cyclohexyl phenyl acetic acid:

This was prepared following the procedure described in J. Amer. Chem. Soc. 75, 2654 (1953).

Step b: Preparation of (1α,5α,6α)-N-[3-benzyl-3-azabicyclo [3.1.0]hexyl-6-(aminomethyl)-yl]-2-hydroxy-2-cyclohexyl-2-phenyl acetamide To a solution of (1α,5α,6α)-6-aminomethyl-3-benzyl-3-azabicyclo[3.1.0]hexane (1 mmol, 0.202 gm) in dimethyl formamide (5 ml) was added 2-hydroxy-2-cyclohexyl-2-phenylacetic acid (1 mmol, 0.234 gm) and cooled to 0° C. The reaction mixture was treated with hydroxy benzotriazole (1 mmol, 0.135 g) followed by N-methyl morpholine (2 mmol, 0.202 gm) and stirred at 0° C. for 0.5 hours. EDC (1 mmol, 0.192 gm) was then added. The reaction mixture (RM) after being stirred at 0° C. for 1 hour was later stirred at RT overnight. The RM was poured into cold water and extracted with ethyl acetate. The organic layer was dried and the crude product obtained after removing the solvent was purified by column chromatography (Silicagel 100-200 mesh) eluting the compound with 30-70 ethyl acetate-hexane mixture.

$^1$H-NMR: (CDCl$_3$) δ—values: 7.61-7.11 (m, 10H), 3.55 (s, 2H), 2.92-2.88 (m, 4H), 2.32-2.29 (m, 2H), 1.37-1.16 (m, 14H)

IR (DCM):1653 cm$^{-1}$

EXAMPLE 3

Preparation of (1α,5α,6α)-N-[3-benzyl-3-azabicyclo [3.1.0]hexyl-6(aminomethyl)-yl]-2-hydroxy-2-cyclopentyl-2-phenyl acetamide (Compound No. 3)

Step a: Preparation of 2-hydroxy-2-cyclopentyl phenyl acetic acid:

This was prepared following the procedure described in J. Amer. Chem. Soc. 75, 2654 (1953).

Step b: Preparation of (1α,5α,6α)-N-[3-benzyl-3-azabicyclo [3.1.0]hexyl-6-(aminomethyl)-yl]-2-hydroxy-2-cyclopentyl-2-phenyl acetamide To a solution of (1α,5α,6α)-6-aminomethyl-3-benzyl-3-azabicyclo[3.1.0]hexane (29.9 mmol, 6.05 gm) in dimethyl formamide (100 ml) was added 2-hydroxy-2-cyclopentyl-2-phenyl acetic acid (27.2 mmol, 6.0 gm) and cooled to 0° C. The reaction mixture was treated with hydroxy benzotriazole (29.9 mmol, 4.04 gm) followed by N-methyl morpholine (54.4 mmol, 5.2 gm) and was stirred at 0° C. for 0.5 hrs. The reaction mixture was poured into saturated bicarbonate solution and extracted with ethyl acetate. The organic layers were washed with water and dried over sodium sulphate and concentrated under reduced pressure. The residue was purified by column chromatography (silicagel 100-200 mesh) eluting compound with 20-80 to 25-75 ethyl acetate-hexane mixture. It gave a compound in 93-95% purity. To obtain higher purity (about 99%) of the compound it was triturated with toluene and filtered.

$^1$H-NMR: (CDCl$_3$) δ—values: 7.61-7.23 (m, 10H), 6.45 (bs,1H), 3.57 (s, 2H), 3.11-2.90 (m, 4H), 2.34-2.31 (m, 2H), 1.68-1.48 (m, 10H), 1.23 (m,2H).

MS: (M+1)=405.3 m.pt. 131-134° C.

IR (DCM): 1647, 1522, 1265 cm$^{-1}$

EXAMPLE 4

Preparation of (1α,5α,6α)-[3-benzyl-3-azabicyclo [3.1.0]hexyl-6-(methyl)-yl]-2-hydroxy-2,2-diphenyl acetate (Compound No. 4)

Step-a: Preparation of (1α,5α,6α)-3-benzyl-6-hydroxymethyl-3-azabicyclo[3.1.0]hexane synthesized as per reported procedure of EP 0 413 455 A2.

Step b: Preparation of (1α,5α,6α)-3-benzyl-6-(methanesulfonyloxy)methyl-3-azabicyclo[3.1.0]hexane:

A solution of the title compound of preparation of Step a of Compound 4 (0.203 g; 1 mmol) and triethylamine (0.21 gms, 2 mmol) in ethyl acetate (25 ml) was cooled to −10° C. and treated with methanesulfonyl chloride (0.17 gms, 1.5 mmol). After stirring for one hour at −10° C., the reaction was poured into a saturated aqueous sodium bicarbonate solution. The organic layer was dried over sodium sulphate. Filtration and removal of the solvent in vacuo provided the title compound as a yellow oil, which was used as such in the following step without further purification.

$^1$H-NMR (CDCl$_3$) δ—values: 7.45 (m, 5 H, arom.), 4.29 (s, 2H), 3.81 (m, 2H), 3.13 (m, 4H), 2.84 (s, 3H), 1.38 (m, 3H)

Step c: Preparation of (1α,5α,6α)-[3-benzyl-3-azabicyclo [3.1.0]hexyl-6-(methyl)-yl]-2-hydroxy-2,2-diphenyl acetate:

To a solution of 2-hydroxy-2,2-diphenyl acetic acid (1 mmol, 0.228 gms) in xylene was added, (1α,5α,6α)-3-benzyl-6-(methanesulfonyloxy)methyl-3-azabicyclo[3.1.0]hexane: (0.28 gms, 1 mmol) followed by DBU (1,8-diazabicyclo [5,4,0]undec-7-ene, (2 mmol, 0.305 gms) and the reaction mixture refluxed for 6 hrs. The reaction mixture was then washed with water, brine and dried over sodium sulphate. The solvents were evaporated and the crude compound thus obtained was purified by column chromatography (silicagel, 100-200 mesh) eluting the compound with 20-80, ethyl acetate hexane mixture.

$^1$H-NMR (CDCl$_3$) δ—values: 7.46-7.22 (m, 15 H. arom.), 4.24 (s, 1H), 4.11-4.09 (d, 2H), 3.56 (s, 2H), 2.91-2.89 (d, 2H), 2.31-2.29 (d, 2H), 1.67-1.62 (m, 1H) 1.3 (s, 2H)

IR (DCM): 1724 cm$^{-1}$

EXAMPLE 5

Preparation of (1α,5α,6α)-[3-benzyl-3-azabicyclo [3.1.0]hexyl-6-(methyl)-yl]-2-hydroxy-2-cyclohexyl-2-phenyl acetate (Compound No. 5)

This compound was prepared following the procedure as in Example 4, step c using 2-hydroxy-2-cyclohexyl phenyl acetic acid instead of 2-hydroxy-2,2-diphenyl acetic acid.

$^1$H-NMR (CDCl$_3$) δ—values: 7.66-7.21 (m, 10 H, arom.), 4.09-3.92 (dd, 2H), 3.69 (s,2H), 2.93-2.89 (m, 2H), 2.33-2.30 (m, 3H), 1.65-1.12 (m, 13H)

IR (DCM): 1720 cm$^{-1}$

EXAMPLE 6

Preparation of (1α,5α,6α)-[3-benzyl-3-azabicyclo [3.1.0]hexyl-6-(methyl)-yl]-2-hydroxy-2-cyclopentyl-2-phenyl acetate (Compound No. 6)

This compound was prepared following the procedure as in Example 4, step c using 2 hydroxy-2-cyclopentyl phenyl acetic acid instead of 2-hydroxy-2,2-diphenyl acetic acid.

$^1$H-NMR (CDCl$_3$) δ—values: 7.67-7.20 (m, 10 H, arom.), 4.06-3.93 (dd, 2H), 3.57 (s,2H), 2.94-2.89 (m, 3H), 2.34-2.30 (m, 2H), 1.63-1.27 (m, 11H)

IR (DCM): 1718 cm$^{-1}$

EXAMPLE 7

Preparation of (1α,5α,6α)-[3-(2-(2,3-dihydrobenzofuran-5-yl)ethyl-3-azabicyclo[3.1.0]hexyl-6(methyl)-yl]-2-hydroxy-2-cyclohexyl-2-phenyl acetate (Compound No. 7)

The compound obtained as in Example 5 was debenzylated and then N-alkylated as given below:

Step a: Preparation of (1α,5α,6α)-[3-azabicyclo[3.1.0] hexyl-6-(methyl)-yl]-2-hydroxy-2-cyclohexyl-2-phenyl acetate A solution of (1α,5α,6α)-N-[3-benzyl-3-azabicyclo [3.1.0]hexyl-6-(methyl)-yl]-2-hydroxy-2-cyclohexyl-2-phenyl acetate (1 mmol) in methanol (50 ml), was added to a suspension of Pd/C (10%, 0.1 gm) and the reaction mixture was hydrogenated in Parr apparatus at 45 psi for 3 hrs. The reaction mixture was filtered and concentrated to afford the title compound.

$^1$H-NMR (CDCl$_3$) δ—values: 7.65-7.15 (m, 5 H, arom.), 4.14-4.02 (dd, 2H), 3.14-2.94-(m, 3H), 2.29-2.21 (m, 2H), 1.46-1.11 (m, 13H)

IR (KBr): 1723 cm$^{-1}$

Step b: Preparation of 5-(2-bromoethyl)-2,3-dihydrobenzo [2,3-b]benzofuran Synthesized as per reported procedure of EP 0 388 054 A1, Step c: To a solution of (1α,5α,6α)-[3-azabicyclo[3.1.0] hexyl-6-methyl)-yl]-2-hydroxy-2-cyclohexyl-2-phenyl acetate (0.329 gms, 1 mmol) in dimethyl formamide (5 ml) was added potassium carbonate (2 mmol 0.276 gms), potassium iodide (1 mmol 0.166 gms) and 5-(2-bromoethyl)-2,3-dihydrobenzo[2,3-b]benzofuran (0.275 gms, 1.2 mmol). The reaction mixture was stirred at room temperature overnight, poured into water and extracted with ethyl acetate. The combined organic layer was washed with water, brine and dried over sodium sulphate. The crude compound obtained after evaporation of the solvent under vacuum was purified by column chromatography (silica gel 100-200 mesh) eluting the compound with 20:80 ethyl acetate:hexane.

$^1$H-NMR (CDCl$_3$) δ—values: 7.67-6.67 (m, 8 H, arom.), 4.56-4.50 (m, 2H), 4.09-3.7-(dd, 2H), 3.19-3.01 (m, 4H), 2.62-2.60 (m, 3H), 2.33-2.30 (m, 4H), 1.65-1.11 (m, 13H)

IR (DCM): 1721 cm$^{-1}$

EXAMPLE 8

Preparation of (1α,5α,6α)-[3-(2-(2,3-dihydrobenzofuran-5yl)ethyl)-3-azabicyclo[3.1.0]hexyl-6-(methyl)-yl]-2-hydroxy-2-cyclopentyl-2-phenyl acetate (Compound No. 8)

The compound obtained as in Example 6 was debenzylated and then N-alkylated as given below:

Step a: Preparation of (1α,5α,6α)-[3-azabicyclo[3.1.0] hexyl-6-(methyl)-yl]-2-hydroxy-2-cyclopentyl-2-phenyl acetate A solution of (1α,5α,6α)-N-[3-benzyl-3-azabicyclo [3.1.0]hexyl-6-methyl)-yl]-2-hydroxy-2-cyclopentyl-2-phenyl acetate (1 mmol) in methanol (50 ml), was added to a suspension of Pd/C (10%, 0.1 gm) and the reaction mixture was hydrogenated in Parr apparatus at 45 psi for 3 hrs. The reaction mixture was filtered and concentrated to afford the title compound.

$^1$H-NMR (CDCl$_3$) δ—values: 7.66-7.26 (m, 5 H, arom.), 4.15-4.01 (dd, 2H), 3.06-2.92-(m, 3H), 2.43-2.36 (m, 2H), 1.61-1.02 (m, 11H)

IR (KBr): 1721 cm$^{-1}$

Step b: To a solution of compound (1α,5α,6α)-[3-azabicyclo [3.1.0]hexyl-6-(methyl)-yl]-2-hydroxy-2-cyclopentyl-2-phenylacetate (0.315 g, 1 mmol) in dimethyl formamide (5 ml) was added potassium carbonate (2 mmol, 0.276 gms), potassium iodide (1 mmol 0.166 gms) and 5-(2-bromoethyl)-2,3-dihydrobenzo[2,3-b]benzofuran (0.275 gms, 1.2 mmol). The reaction mixture was stirred at room temperature overnight, poured into water and extracted with ethyl acetate. The combined organic layer was washed with water, brine and dried over sodium sulphate. The crude compound obtained after evaporation of the solvent under vacuum was purified by column chromatography (silica gel 100-200 mesh) eluting the compound with 20:80 ethyl acetate:hexane.

$^1$H-NMR (CDCl$_3$) δ—values: 7.68-6.67 (m, 8 H, arom.), 4.56-4.50 (m, 2H), 4.07-3.97-(dd, 2H), 3.19-3.02 (m, 4H), 2.33-2.30 (m, 6H), 1.37-1.25 (m, 11H)

IR (DCM): 1719 cm$^{-1}$

EXAMPLE 9

Preparation of (1α,5α,6α)-N-[3-(2-(2,3-dihydrobenzofuran-5-yl)ethyl)-3-azabicyclo[3.1.0]hexyl-6-(amino methyl)-yl]-2-hydroxy-2-cyclohexyl-2-phenyl acetamide (Compound No. 9)

The compound obtained as in Example 2 was debenzylated and then N-alkylated as given below:

Step a: Preparation of (1α,5α,6α)-N-[3-azabicyclo[3.1.0] hexyl-6-(aminomethyl)-yl]-2-hydroxy-2-cyclohexyl-2-phenyl acetamide.

A solution of (1α,5α,6α)-N-[3-benzyl-3-azabicyclo [3.1.0]hexyl-6-(aminomethyl)-yl]-2-hydroxy-2-cyclohexyl-2-phenyl acetamide (1 mmol) in methanol (50 ml), was added to a suspension of Pd/C (10%, 0.1 gm) and the reaction mixture was hydrogenated in Parr apparatus at 45 psi for 3 hrs. The reaction mixture was filtered and concentrated to afford the title compound.

$^1$H-NMR (CDCl$_3$) δ—values: 7.62-7.26 (m, 5 H, arom.), 3.15-3.09 (m, 3H), 2.95-2.81-(m, 4H), 1.71-1.2 (m, 13H)

IR (KBr): 1656 cm$^{-1}$

Step b: To solution of compound (1α,5α,6α)-N-[3-azabicyclo[3.1.0]hexyl-6-(aminomethyl)-yl]-2-hydroxy-2-cyclohexylphenyl acetamide (0.328, 1 mmol) in dimethyl formamide (5 ml) was added potassium carbonate (2 mmol 0.276 gms), potassium iodide (1 mmol 0.166 gms) and 5-2-bromoethyl)-2,3-dihydrobenzo[2,3-b]benzofuran (0.275 gms, 1.2 mmol). The reaction mixture was stirred at room temperature overnight, poured into water and extracted with ethyl acetate. The combined organic layer was washed with water, brine and dried over sodium sulphate. The crude compound obtained after evaporation of the solvent under vacuum was purified by column chromatography (silica gel 100-200 mesh) eluting the compound with 20:80 ethyl acetate:hexane.

$^1$H-NMR (CDCl$_3$) δ—values: 7.62-6.64 (m, 8H, arom.), 4.56-4.51 (t, 2H), 3.19-2.31 (m, 12H), 1.70-1.13 (m, 14H)

IR (DCM): 1654 cm$^{-1}$ (amide carbonyl)

EXAMPLE 10

Preparation of (1α,5α,6α)-N-[3-(2-(2,3-dihydrobenzofuran-5-yl)ethyl)-3-azabicyclo[3.1.0]hexyl-6-(aminomethyl)-yl]-2-hydroxy-2-cyclopentyl-2-phenyl acetamide (Compound No. 10)

The compound obtained as in Example 3 was debenzylated and then N-alkylated as given below:

Step a: Preparation of (1α,5α,6α)-N-[3-azabicyclo[3.1.0]hexyl-6-(aminomethyl)-yl]-2-hydroxy-2-cyclopentyl-2-phenyl acetamide A solution of (1α,5α,6α)-N-[3-benzyl-3-azabicyclo[3.1.0]hexyl-6-(aminomethyl)-yl]-2-hydroxy-2-cyclopentyl-2-phenyl acetamide (1 mmol) in methanol (50 ml), was added to a suspension of Pd/C (10%, 0.1 gm) and the reaction mixture was hydrogenated in Parr apparatus at 45 psi for 3 hrs. The reaction mixture was filtered and concentrated to afford the title compound.

$^1$H-NMR (CDCl$_3$) δ—values: 7.62-7.23 (m, 5 H, arom.), 3.13-3.07 (m, 2H), 2.95-2.81 (m, 5H), 1.34-0.87 (m, 11H)

IR (KBr): 1655 cm$^{-1}$

Step b: To a solution of compound (1α,5α,6α)-N-[3-azabicyclo[3.1.0]hexyl-6-(aminomethyl)-yl]-2-hydroxy-2-cyclopentyl-2-phenylacetamide (0.314 g, 1 mmol) in dimethyl formamide(5 ml) was added potassium carbonate (2 mmol 0.276 gms), potassium iodide (1 mmol 0.166 gms) and 5-(2-bromoethyl)-2,3-dihydrobenzo[2,3-b]benzofuran (0.275 gms, 1.2 mmol). The reaction mixture was stirred at room temperature overnight, poured into water and extracted with ethyl acetate. The combined organic layer was washed with water, brine and dried over sodium sulphate. The crude compound obtained after evaporation of the solvent under vacuum was purified by column chromatography (silica gel 100-200 mesh) eluting the compound with 20:80 ethyl acetate:hexane.

$^1$H-NMR (CDCl$_3$) δ—values: 7.62-6.67 (m, 8H, arom.), 4.56-4.51 (t, 2H), 3.19-2.29 (m, 12H), 1.70-1.11 (m, 12H)

IR (KBr): 1657 cm$^{-1}$

EXAMPLE 11

Preparation of (1α,5α,6α)-[3-(2-(3,4-methylenedioxyphenyl)ethyl)-3-azabicyclo[3.1.0]hexyl-6-(methyl)-yl]-2-hydroxy-2-cyclopentyl-2-phenyl acetate (Compound No. 11)

Step a: Preparation of 3,4-methylenedioxyphenethyl bromide Synthesized as Per Reported Procedure of EP 0 388 054 A1

Step b: This compound was prepared following the procedure as in Example 8, step b, using 3,4-methylenedioxyphenethyl bromide instead of 5-(2-bromoethyl)-2,3-dihydrobenzo[2,3-b]benzofuran.

$^1$H-NMR (CDCl$_3$) δ—values: 7.8-6.6 (m, 8H, arom.), 6.0 (s, 2M), 4.2-3.9 (dd, 2H), 3.2-2.3 (m, 9H), 1.7-1.1 (m, 11H)

IR (DCM): 1720 cm$^{-1}$

EXAMPLE 12

Preparation of (1α,5α,6α)-[3-(2-(3,4methylenedioxyphenyl)ethyl)-3-azabicyclo[3.1.0]hexyl-6-(methyl)-yl]-2-hydroxy-2-cyclohexyl-2-phenyl acetate (Compound No. 12)

This compound was prepared following the procedure as in Example 7, step c, using 3,4-methylenedioxyphenethyl bromide instead of 5-(2-bromoethyl)-2,3-dihydrobenzo[2,3-b]benzofuran.

$^1$H-NMR (CDCl$_3$) δ—values: 7.67-6.6 (m, 8H, arom.), 5.91 (s, 2H), 4.09-3.92 (dd, 2H), 3.03-2.99 (m, 2H), 2.61-2.59 (m, 4H), 2.32-2.28 (m, 4H) 1.65-1.1 (m, 12H).

IR (DCM): 1721 cm$^{-1}$

EXAMPLE 13

Preparation of (1α,5α,6α)-N-[3-(2-(3,4-methylenedioxyphenyl)ethyl)-3-azabicyclo[3.1.0]hexyl-6-(aminomethyl)-yl]-2-hydroxy-2-cyclopentyl-2-phenyl acetamide (Compound No. 13)

This compound was prepared following the procedure as in Example 10, Step b using 3,4-methylenedioxyphenethyl bromide instead of 5-(2-bromoethyl)-2,3-dihydrobenzo[2,3-b]benzofuran.

$^1$H-NMR (CDCl$_3$) δ—values: 7.61-6.59 (m, 8H, arom.), 5.91 (s, 2H), 3.05-2.27 (m, 11H), 1.66-1.24 (m, 11H)

IR (KBr): 1657 cm$^{-1}$

EXAMPLE 14

Preparation of (1α,5α,6α)-N-[3-(2-(3,4-methylenedioxyphenyl)ethyl)-3-azabicyclo[3.1.0]hexyl-6-(aminomethyl)-yl]-2-hydroxy-2-cyclohexyl-2-phenyl acetamide (Compound No. 14)

This compound was prepared following the procedure as in Example 9, Step b using 3,4-methylenedioxyphenethyl bromide instead of 5-(2-bromoethyl)-2,3-dihydrobenzo[2,3-b]benzofuran.

$^1$H-NMR (CDCl$_3$) δ—values: 7.62-6.59 (m, 8H, arom.), 5.91 (s, 2H), 3.10-2.33 (m, 11H), 1.70-1.17 (m, 13H)

IR (DCM): 1653 cm$^{-1}$

EXAMPLE 15

Preparation of (1α,5α,6α)-N-[3-(4-methyl-3-pentenyl)-3-azabicyclo[3.1.0]hexyl-6-(aminomethyl)-yl]-2-hydroxy-2-cyclohexyl-2-phenyl acetamide (Compound No. 15)

This compound was prepared following the procedure as in Example 9, Step b using 5-bromo-2-methyl-2-pentene instead of 5-(2-bromoethyl)-2,3-dihydrobenzo[2,3-b]benzofuran.

¹H-NMR (CDCl₃) δ—values: 7.61-6.26 (m, 5H, arom.), 5.06 (t, 1H), 2.99-2.04 (m, 12H), 1.67-1.22 (m, 19H)

IR (DCM): 1656 cm⁻¹

EXAMPLE 16

Preparation of (1α,5α,6α)-N-[3-(4-methyl-3-pentenyl)-3-azabicyclo[3.1.0]hexyl-6-(aminomethyl)-yl]-2-hydroxy-2-cyclopentyl-2-phenyl acetamide (Compound No. 16)

This compound was prepared following the procedure as in Example 10, Step b using 5-bromo-2-methyl-2-pentene instead of 5-(2-bromoethyl)-2,3-dihydrobenzo[2,3-b]benzofuran.

¹H-NMR (CDCl₃) δ—values: 7.61-7.25 (m, 5H, arom.), 5.06 (t, 1H), 3.06-2.04 (m, 12H), 1.67-1.1 (m, 16H)

IR (DCM): 1652 cm⁻¹

EXAMPLE 17

Preparation of (1α,5α,6α)-[3-(4-methyl-3-pentenyl)-3-azabicyclo[3.1.0]hexyl-6-(methyl)-yl]-2-hydroxy-2-cyclohexyl-2-phenyl acetate (Compound No. 17)

This compound was prepared following the procedure as in Example 7, Step c using 5-bromo-2-methyl-2-pentene instead of 5-(2-bromoethyl)-2,3-dihydrobenzo[2,3-b]benzofuran ¹H-NMR (CDCl₃) δ—values: 7.66-7.22 (m, 5H, arom.), 5.08 (t, 1H), 4.1-3.92 (dd, 2H), 3.0-2.97 (m, 2H), 2.27-2.08 (m, 7H), 1.65-1.11 (m, 19H)

IR (DCM): 1721 cm⁻¹

EXAMPLE 18

Preparation of (1α,5α,6α)-[3-(4methyl-3-pentenyl)-3-azabicyclo[3.1.0]hexyl-6-(methyl)-yl]-2-hydroxy-2-cyclopentyl-2-phenyl acetate (Compound No. 18)

This compound was prepared following the procedure as in Example 8, Step b using 5-bromo-2-methyl-2-pentene instead of 5-(2-bromoethyl)-2,3-dihydrobenzo[2,3-b]benzofuran.

¹H-NMR (CDCl₃) δ—values: 7.67-7.26 (m, 5H, arom.), 5.07 (t, 1H), 4.09-3.94 (dd, 2H), 3.01-2.08 (m, 9H), 1.68-0.97 (m, 17H)

IR (DCM): 1720 cm⁻¹

EXAMPLE 19

Preparation of (1α,5α,6α)-[3-(1-phenylethyl)-3-azabicyclo[3.1.0]hexyl-6-(methyl)-yl]-2-hydroxy-2-cyclopentyl-2-phenyl acetate (Compound No. 19)

This compound was prepared following the procedure as in Example 8, Step b using (1-bromoethyl)benzene instead of 5-(2-bromoethyl)-2,3-dihydrobenzo[2,3-b]benzofuran.

¹H-NMR (CDCl₃) δ—values: 7.67-7.25 (m, 10H, arom.), 4.06-3.93 (dd, 2H), 3.24-2.08 (m, 6H), 1.6-1.23 (m, 15H)

IR (DCM): 1719 cm⁻¹

EXAMPLE 20

Preparation of (1α,5α,6α)-[3-(1-phenylethyl)-3-azabicyclo[3.1.0]hexyl-6-(methyl)-yl-]-2-hydroxy-2-cyclohexyl-2-phenyl acetate (Compound No. 20)

This compound was prepared following the procedure as in Example 7, Step c using (1-bromoethyl)benzene instead of 5-(2-bromoethyl)-2,3-dihydrobenzo[2,3-b]benzofuran.

¹H-NMR (CDCl₃) δ—values: 7.67-7.18 (m, 10H, arom.), 4.09-3.7 (dd, 2H), 3.24-2.11 (m, 4H), 2.63-2.37 (m, 8H), 1.64-1.1 (m, 11H)

IR (DCM): 1720 cm⁻¹

EXAMPLE 21

Preparation of (1α,5α,6α)-N-[3-(1-phenylethyl)-3-azabicyclo[3.1.0]hexyl-6-(aminomethyl)-yl]-2-hydroxy-2-cyclohexyl-2-phenyl acetamide (Compound No. 21)

This compound was prepared following the procedure as in Example 9, Step b using (1-bromoethyl)benzene instead of 5-(2-bromoethyl)-2,3-dihydrobenzo[2,3-b]benzofuran.

¹H-NMR (CDCl₃) δ—values: 7.66-7.20 (m, 10H, arom.), 3.29-2.09 (m, 9H), 1.69-0.88 (m, 16H)

IR (KBr): 1653 cm⁻¹

EXAMPLE 22

Preparation of (1α,5α,6α)-N-[3-(1-phenylethyl)-3-azabicyclo[3.1.0]hexyl-6-(aminomethyl)-yl]-2-hydroxy-2-cyclopentyl-2-phenyl acetamide (Compound No. 22)

This compound was prepared following the procedure as in Example 10, Step b using (1-bromoethyl)benzene instead of 5-(2-bromoethyl)-2,3-dihydrobenzo[2,3-b]benzofuran.

¹H-NMR (CDCl₃) δ—values: 7.61-7.26 (m, 10H, arom.), 3.26-2.07 (m, 9H), 1.67-1.15 (m, 13H)

IR (DCM): 1651 cm⁻¹

EXAMPLE 23

Preparation of (1α,5α,6α)-N-[3-benzyl-3-azabicyclo[3.1.0]hexyl-6-(1-aminoethyl)-yl]-2-hydroxy-2,2-diphenyl acetamide (Compound No. 23)

Step a: Preparation of (1α,5α,6α)-6-(1-hydroxyethyl)-3-benzyl-3-azabicyclo[3.1.0]hexane: (1α,5α,6α)-3-benzyl-3-azabicyclo[3.1.0]hexane-6-carboxaldehyde (synthesized as per reported procedure of EP 0 413 455 A2, 2 gm, 100 mmol) was dissolved in tetrahydrofuran (400 ml) and cooled to −70° C. Methyllithium (105 mL of a 0.98 M solution in ether, 102 mmol) was added dropwise, stirred for one hour and later allowed to attain room temperature. Saturated aqueous ammonium chloride was added to the reaction mixture, the mixture was then extracted with ethyl acetate. The combined organic layers were dried over sodium sulphate, filtered and concentrated in vacuo to provide the product as a brown oil (yield 1.68 gm).

¹H-NMR (CDCl₃) δ—values: 7.26 (m, 5H, arom.), 3.59 (s, 2H), 3.16 (m, 1H), 2.97 (m, 2H), 2.35 (m, 2H), 1.39 (m, 1H), 1.24 (m, 5H)

Step b: Preparation of (1α,5α,6α)-3-benzyl-3-azabicyclo[3.1.0]hexane-6-methylketone Dimethylsulphoxide (1.65 ml, 23 mmol) was added to a solution of oxalyl chloride (1.1 ml, 12.65 mmol) in methylene chloride (350 ml) maintained at −70° C. A solution of the title compound of preparation step a (2.5 gm, 11.5 mmol) in methylene chloride (50 ml) was then added to the reaction mixture at −70° C. After the addition of triethylamine (6.4 ml, 46 mmol), the mixture was allowed to warm to room temperature, water was added and the organic layer was collected, dried over sodium sulphate, filtered and concentrated to provide a light brown oil. Column chromatography (eluant: 20% ethyl acetate in hexane) provided the title compound (yield 1.4 gms).

$^1$H-NMR (CDCl$_3$) δ—values: 7.27 (m, 5H, arom.), 3.6 (s, 2H), 3.016 (m, 2H), 2.41 (m, 3H), 2.23 (s, 3H), 1.17 (m, 2H)

IR (DCM): 1694 cm$^{-1}$

Step c: Preparation of (1α,5α,6α)-6-(1-aminoethyl)-3-benzyl-3-azabicyclo[3.1.0]hexane To a stirred solution of the title compound of preparation step b (1.2 gms, 5.5 mmol) and ammonium acetate (1.28 gms, 16.6 mmol) in methanol (50 ml) was added sodium cyanoborohydride (0.87 gms, 43.75 mmol) at room temperature. The mixture was stirred for 18 hours at the same temperature. After the addition of saturated aqueous sodium bicarbonate, methanol was evaporated and the mixture was extracted three times with dichloromethane (100 ml). The combined organic extract was dried over sodium sulphate, filtered and concentrated under vacuo to obtain the crude compound (yield: 0.8 gms) which was used in the next step without purification.

$^1$H-NMR (CDCl$_3$) δ—values: 7.26 (m, 5H, arom.), 3.57 (s, 2H), 2.97 (m, 2H), 2.33 (m, 2H), 2.2 (m, 1H), 1.29 to 1.13 (m, 6H)

IR (DCM): 1654 cm$^{-1}$

Step d: Preparation of (1α,5α,6α)-N-[3-benzyl-3-azabicyclo[3.1.0]hexyl-6-(1-aminoethyl)-yl]-2-hydroxy-2,2-diphenyl acetamide:

The compound of Step-d was prepared by following the procedure described in step-c of Example 1 using (1α,5α,6α)-6-(1-aminoethyl)-3-benzyl-3-azabicyclo[3.1.0]hexane instead of (1α,5α,6α)-6-aminomethyl-3-benzyl-3-azabicyclo[3.1.0]hexane.

$^1$H-NMR (CDCl$_3$) δ—values: 7.33 (m, 15H. arom.), 6.16 (m, 1H), 3.56 (m, 2H), 3.43 (m, 1H), 2.88 (m, 2H), 2.31 (m, 2H), 1.40 (m, 1H), 1.29 to 1.13 (m, 5H)

IR (DCM): 1656 cm$^{-1}$

EXAMPLE 24

Preparation of (1α,5α,6α)-N-[3-benzyl-3-azabicyclo[3.1.0]hexyl-6-(1-aminoethyl)-yl]-2-hydroxy-2-cyclohexyl-2-phenyl acetamide (Compound No. 24)

This compound was prepared by following the procedure described in Step-b of Example 2, using (1α,5α,6α)-6-(1-aminoethyl)-3-benzyl-3-azabicyclo[3.1.0]hexane instead of (1α,5α,6α)-6-aminomethyl-3-benzyl-3-azabicyclo[3.1.0]hexane.

$^1$H-NMR (CDCl$_3$) δ—values: 7.59 to 7.09 (m, 10H, arom.), 6.52 (m, 1H), 3.55 (m, 2H), 3.25 (m, 1H), 2.90 (m, 2H), 2.25 (m, 3H), 1.37 to 0.85 (m, 16H)

IR (DCM): 1651 cm$^{-1}$

EXAMPLE 25

Preparation of (1α,5α,6α)-N-[3-benzyl-3-azabicyclo[3.1.0]hexyl-6-(1-aminoethyl)-yl]-2-hydroxy-2-cyclopentyl-2-phenyl acetamide (Compound No. 25)

This compound was prepared by following the procedure described in Step-b of Example 3, using (1α,5α,6α)-6-(1-aminoethyl)-3-benzyl-3-azabicyclo[3.1.0]hexane instead of (1α,5α,6α)-6-aminomethyl-3-benzyl-3-azabicyclo[3.1.0]hexane.

$^1$H-NMR (CDCl$_3$) δ—values: 7.59 to 7.23 (m, 10H, arom.), 6.30 (m, 1H), 3.54 (s, 2H), 3.29 (m, 1H), 2.93 to 2.79 (m, 3H), 2.27 (m, 3H), 1.40 (m, 1H), 1.28 to 1.0 (m, 14H)

IR (DCM): 1651 cm$^{-1}$

EXAMPLE 26

Preparation of (1α,5α,6α)-[3-(3-methyl-2-butenyl)-3-azabicyclo[3.1.0]hexyl-6-(methyl)-yl]-2-hydroxy-2-cyclohexyl-2-phenyl acetate (Compound No. 26)

This compound was prepared following the procedure as in Example 7, Step c using 1-bromo-3-methylbut-2-ene instead of 5-(2-bromoethyl)-2,3-dihydrobenzo[2,3-b]benzofuran.

$^1$H-NMR (CDCl$_3$) δ—values: 7.66-7.23 (m, 5H, arom.), 5.19 (t, 1H), 4.08-3.89 (dd, 2H), 3.7 (s, 1H), 3.029-2.94 (m, 4H), 2.3-2.27 (m, 3H), 1.71-1.11 (m, 19H)

IR (DCM): 1721 cm$^{-1}$

EXAMPLE 27

Preparation of (1α,5α,6α)-[3-(3-methyl-2-butenyl-3-azabicyclo[3.1.0]hexyl-6-(methyl)-yl]-2-hydroxy-2-cyclopentyl-2-phenyl acetate (Compound No. 27)

This compound was prepared following the procedure as in Example 8, Step b using 1-bromo-3-methylbut-2-ene instead of 5-(2-bromoethyl)-2,3-dihydrobenzo[2,3-b]benzofuran.

$^1$H-NMR (CDCl$_3$) δ—values: 7.67-7.23 (m, 5H, arom.), 5.19 (t, 1H), 4.05-3.91 (dd, 2H), 3.76 (s, 1H), 3.039-2.96 (m, 4H), 2.31-2.28 (m, 3H), 1.71-1.25 (m, 17H)

IR (DCM): 1721 cm$^{-1}$

EXAMPLE 28

Preparation of (2R)-(+)-(1α,5α,6α)-N-[3-benzyl-3-azabicyclo[3.1.0]hexyl-6-(aminomethyl)-yl]-2-hydroxy-2-cyclohexyl-2-phenyl acetamide (Compound No. 28)

Step a: Preparation of (2R)-(−)-2-hydroxy-2-cyclohexyl-2-phenyl acetic acid:

Synthesized as per reported procedure of Paul T. Grover, et. al. J. Org. Chem. 2000, 65, 6283-6287

Step b: The title compound was synthesised following the procedure as in step-b of Example 2, using (2R)-(−)-2-hydroxy-2-cyclohexyl-2-phenylacetic acid instead of 2-hydroxy-2-cyclohexyl-2-phenylacetic acid.

$^1$H-NMR (CDCl$_3$) δ—values: 7.61-7.22 (m, 10H, arom.), 6.62 (m, 1H), 3.55 (s, 2H), 3.26-2.07 (m, 9H), 1.67-1.15 (m, 13H)

$[α]^{25±3° C.}$=+3.85° (0.9846% MeOH)

IR (DCM): 1651 cm$^{-1}$

EXAMPLE 29

Preparation of (2R)-(+)-(1α,5α,6α)-N-[3-benzyl-3-azabicyclo[3.1.0]hexyl-6-(aminomethyl)-yl]-2-hydroxy-2-cyclopentyl-2-phenyl acetamide (Compound No. 29)

Step a: Preparation of (2R)-(−)-2-hydroxy-2-cyclopentyl-2-phenyl acetic acid:

Synthesized as per reported procedure of Paul T. Grover, et. al. J. Org. Chem. 2000, 65, 6283-6287.

Step b: The title compound was synthesised following the procedure in step-b of Example 3, using (2R)-(−)-2hydroxy-2-cyclopentyl-2-phenyl acetic acid instead of 2-hydroxy-2-cyclopentyl-2-phenylacetic acid.

$^1$H-NMR (CDCl$_3$) δ—values: 7.61-7.26 (m, 10H, arom.), 3.26-2.07 (m, 9H), 1.67-1.15 (m, 13H)

IR (DCM): 1651 cm$^{-1}$ $[α]^{25° C.}$=+3.95° (0.936% MeOH)

EXAMPLE 30

Preparation of (2R)(+)-(1α,5α,6α)-[3-benzyl-3-azabicyclo[3.1.0]hexyl-6-(methyl)-yl]-2-hydroxy-2-cyclohexyl-2-phenyl acetate (Compound No. 30)

Step a: Preparation of (2R)(−)2-hydroxy-2-cyclohexyl-2-phenyl acetic acid:

Synthesized as per reported procedure of Paul T. Grover, et. al. J. Org. Chem. 2000, 65, 6283-6287.

Step b: The title compound was synthesized following the procedure as in Example 4, step c using (2R)(−)-2-hydroxy-2-cyclohexyl-2-phenyl acetic acid instead of 2-hydroxy-2,2-diphenyl acetic acid.

$^1$H-NMR (CDCl$_3$) δ—values: 7.61-7.26 (m, 10H, arom.), 3.26-2.07 (m, 9H), 1.67-1.15 (m, 13H)

IR (DCM): 1651 cm$^{-1}$ $[α]^{25° C.}$=+9.8° (1.09% MeOH)

EXAMPLE 31

Preparation of (2R)(+)-(1α,5α,6α)-[3-benzyl-3-azabicyclo[3.1.0]hexyl-6-(methyl)-yl]-2-hydroxy-2-cyclopentyl-2-phenyl acetate (Compound No. 31)

Step a: Preparation of (2R)(−)2-hydroxy-2-cyclopentyl-2-phenyl acetic acid:

Synthesized as per reported procedure of Paul T. Grover, et. al. J. Org. Chem. 2000, 65, 6283-6287.

Step b: The title compound was synthesised following the procedure as in Example 4, step c using (2R)(−)-2-hydroxy-2-cyclopentyl-2-phenylacetic acid instead of 2-hydroxy-2,2-diphenyl acetic acid.

$^1$H-NMR (CDCl$_3$) δ—values: 7.67-7.2 (m, 10H, arom.), 4.06 (m, 1H), 3.93 (m, 1H), 3.74 (s, 2H), 2.94-2.89 (m, 3H), 2.33-2.3 (m, 2H), 1.64-1.29 (m, 11H)

IR (DCM): 1719 cm$^{-1}$ $[α]$=+14.8° (1% MeOH)

EXAMPLE 32

Preparation of (2S)-(−)(1α,5α,6α)-N-[3-benzyl-3-azabicyclo[3.1.0]hexyl-6-(aminomethyl)-yl]-2-hydroxy-2-cyclopentyl-2-phenyl acetamide (Compound No. 32)

Step a: Preparation of (2S)(+)2-hydroxy-2-cyclopentyl-2-phenyl acetic acid:

Synthesized as per reported procedure of Paul T. Grover, et. al. J. Org. Chem. 2000, 65, 6283-6287.

Step b: The title compound was synthesised following the procedure in step-b of Example 3.

$^1$H-NMR (CDCl$_3$) δ—values: 7.62-7.25 (m, 10H. arom.), 6.45 (m, 1H), 3.58 (s, 2H), 3.07-2.92 (m, 5H), 2.35 (m, 2H), 1.77-1.24 (m, 11H)

IR (DCM): 1651 cm$^{-1}$ $[α]$=−2.09° (1.1% MeOH)

EXAMPLE 33

Preparation of (2S)-(−)-(1α,5α,6α)-[3-benzyl-3-azabicyclo[3.1.0]hexyl-6-(methyl)-yl]-2-hydroxy-2-cyclopentyl-2-phenyl acetate (Compound No. 33)

Step a: Preparation of (2S)(+)2-hydroxy-2-cyclopentyl-2-phenyl acetic acid:

Synthesized as per reported procedure of Paul T. Grover, et. al. J. Org. Chem. 2000, 65, 6283-6287.

Step b: The title compound was synthesized following the procedure as in Example 4, Step c using 2S-(−)-2-hydroxy-2-cyclopentyl-2-phenylacetic acid instead of 2-hydroxy-2,2-diphenyl acetic acid.

$^1$H-NMR (CDCl$_3$) δ—values: 7.67-7.2 (m, 10H, arom.), 4.06 (m, 1H), 3.93 (m, 1H), 3.58 (s, 2H), 2.94-2.9 (m, 3H), 2.33-2.31 (m, 2H), 1.66-1.19 (m, 11H)

IR (DCM): 1720 cm$^{-1}$ $[α]$=−14.9° (1.1% MeOH)

EXAMPLE 34

Preparation of (1α,5α,6α)-N-[3-benzyl-3-azabicyclo[3.1.0]hexyl-6-(aminomethyl)-yl]-2-hydroxy-2-cyclopentyl-2-phenyl acetamide L-(+)-tartrate salt (Compound No. 34)

(1α,5α,6α)-N-[3-benzyl-3-bicyclo[3.1.0]hexyl-6-(aminomethyl)-yl]-2-hydroxy-2-cyclopentyl-2-phenyl acetamide (Compound No 3, 1 mmol) was dissolved in ethanol (10 ml) and a solution of L-(+)-tartaric acid (1 mmol) in ethanol (5 ml) was added and stirred at 60° C. for 1 hr. The reaction mixture was then concentrated by the evaporation of solvents under reduced pressure. The resulting solid was triturated with diethyl ether and diethyl ether was removed under reduced pressure to afford the title compound as a white solid.

$^1$H-NMR (CDCl$_3$) δ—values: 7.86 (dd, 1H, Ar—H), 7.56 (dd, 2H, Ar—H), 7.33-7.16 (m, 7H,Ar—H), 5.5(bs,1H),3.76 (s,2H,benzylic), 2.97-2.77 (m, 5H), 2.50-2.45 (m, 2H), 1.50-1.22 (m, 13H)

IR (KBr): 1735 cm$^{-1}$, 1653 cm$^{-1}$

MS: [404.8]; HPLC (99% pure).

EXAMPLE 35

Preparation of (2R)-(+)-(1α,5α,6α)-N-[3-benzyl-3-azabicyclo[3.1.0]hexyl-6-(aminomethyl)-yl]-2-hydroxy-2-cyclopentyl-2-phenylacetamide. L(+)-tartrate salt (Compound No. 35)

2(R)-(+)-(1α,5α,6α)-N-[3-benzyl-3-azabicyclo[3.1.0] hexyl-6-(aminomethyl)-yl]-2-hydroxy-2-cyclopentyl-2-phenylacetamide (Compound No. 29, 1 mmol) was dissolved in methanol (10 ml)and L(+)-tartaric acid was added and stirred at 60° C. for 1 hr. The reaction mixture was concentrated under reduced pressure, the resulting solid was triturated with diethylether and it was filtered off m.p.: 95° C., starts decomposing
IR(KBr):1735 cm$^{-1}$,1655 cm$^{-1}$.
HPLC:99% ee
$[\alpha]^{25° C.}=+10°$ (1.02% MeOH)

EXAMPLE 36

(2S)-(−)-(1α,5α,6α)-N-[3 -benzyl-3 -azabicyclo[3.1.0]hexyl-6-(aminomethyl)-yl]-2-hydroxy-2-cyclopentyl-2-phenylacetamide.L(+)-tartrate salt (Compound No. 35)

(2S)-(−)-(1α,5α,6α)-N-[3-benzyl-3-azabicyclo[3.1.0]hexyl-6-(aminomethyl)-yl]-2-hydroxy-2-cyclopentyl-2-phenylacetamide (Compound 32, 1 mmol) was dissolved in ethanol (10 ml) and a solution of L(+)tartaric acid (1 mmol) in ethanol was added and stirred at 60° C. for 1 hr. The reaction mixture was then concentrated by evaporation of solvents under reduced pressure. Dichloromethane was added to remove last traces of ethanol and to give a solid.

m.p.: −56° C.
IR (KBr):1739 cm$^{-1}$, 1653 cm$^{-1}$

EXAMPLE 37

Preparation of (1α,5α,6α)-N-[3-benzyl-3-azabicyclo[3.1.0]hexyl-6-(aminomethyl)-yl]-2hydroxy-2-cyclobutyl-2-phenylacetamide (Compound No. 37)

Step a: Preparation of 2-hydroxy-2-cyclobutyl-2-phenyl acetic acid synthesised as per reported procedure of Saul B. Kadin and Joseph G. Cannon. J. Org. Chem., 1962, 27, 240-245.

Step b: Preparation of (1α,5α,6α)-N-[3-benzyl-3-azabicyclo [3.1.0]hexyl-6-(aminomethyl)-yl]-2-hydroxy-2-cyclobutyl-2-phenylacetamide.

The compound of step b was prepared by following the procedure in step c of Example 1, using 2-hydroxy-2-cyclobutyl-2-phenyl acetic acid instead of 2-hydroxy-2,2-diphenyl acetic acid.

$^{1}$H NMR(CDCl$_{3}$) δ—values: 7.50-7.22 (m, 10H, Aromatic),6.22(s, 1H), 3.55-1.22 (m, 19H).

EXAMPLE 38

Preparation of (1α,5α,6α)-N-[3-benzyl-3-azabicyclo[3.1.0]hexyl-6-(aminomethyl)-yl]-2-hydroxy-2-cyclopropyl-2-phenylacetamide (Compound No. 38)

Step a: Preparation of 2-hydroxy-2-cyclopropyl-2-phenyl acetic acid.

Synthesised as per reported procedure of Saul B. Kadin and Joseph G. Cannon. J. Org. Chem., 1962,27,240-245.

Step b: Preparation of (1α,5α,6α)-N-[3-benzyl-3-azabicyclo [3.1.0]hexyl-6-(aminomethyl)-yl]-2-hydroxy-2-cyclopropyl-2-phenylacetamide.

The title compound was prepared by following the procedure described in step-c of Example 1, using 2-hydroxy-2-cyclopropyl phenylacetic acid instead of 2-hydroxy-2,2-diphenylacetic acid.

$^{1}$H-NMR(CDCl$_{3}$) δ—values: 7.63-7.23(m, 10H, aromatic), 6.11(s,1H),3.56(s,2H), 3.14-2.04(m,6H),1.59-1.25 (m,10H).

EXAMPLE 39

Preparation of (1α,5α,6α)-N-[3-(3-methyl-2-butenyl)-3-azabicyclo[3.1.0]hexyl-6-(aminomethyl)yl]-2-hydroxy-2-cyclohexyl-2-phenylacetamide (Compound No. 39)

The compound was prepared by using the procedure in Example 9, step b, using 1-bromo-3-methylbut-2-ene instead of 5-(2-bromoethyl)-2,3-dihydrobenzo[2,3-b]benzofuran.

$^{1}$H-NMR (CDCl$_{3}$) δ—values: 7.66-7.02(m,5H,Aromatic), 5.49(t,1H), 3.65-2.87 (m, 9H), 1.86-0.87 (m, 19H)

EXAMPLE 40

Preparation of (1α,5α,6α)-[3-(3,4-methylenedioxyphenyl)methyl-3-azabicyclo[3.1.0]hexyl-6(methyl)-yl]-2-hydroxy-2-cyclopentyl-2-phenylacetate (Compound No. 40)

Step a: Preparation of 3,4-methylenedioxy benzyl bromide.

Phosphorus tribromide (0.35 mmol) was added to a solution of 3,4-methylenedioxy benzyl alcohol (1 mmol) in 10 ml of carbon tetrachloride at room temperature. The reaction mixture was refluxed for 4 hrs., cooled to room temperature and washed with sodium carbonate solution (10 ml). The organic layer was dried and concentrated under reduced pressure to give the required product which was used as such for the next step.

Step b: (1α,5α,6α)-[3-(3,4-methylenedioxyphenyl)methyl-3-azabicyclo[3.1.0]hexyl-6-(methyl)-yl]-2-hydroxy-2-cyclopentyl-2-phenylacetate.

The title compound was prepared using the procedure in Example 8, step b, using 3,4-methylenedioxy benzyl bromide instead of 5-(2-bromoethyl)-2,3-dihydrobenzo[2,3-b]benzofuran.

$^{1}$H-NMR (CDCl$_{3}$) δ—values: 7.67-6.67(m, 8H, aromatic), 5.94(s,2H),4.10-3.92(dd,2H), 3.71(s,1H),3.47(s,2H),2.91-2.87(m,2H),2.30-2.27(m,3H),1.64-1.12 (m, 13H)
IR (DCM): 1720 cm$^{-1}$

EXAMPLE 41

Preparation of (1α,5α,6α)-[3-(2-(3,4-methylenedioxyphenyl)ethyl)-3-azabicyclo[3.1.0]hexyl-6-(methyl)yl]-2-hydroxy-2-cyclopentyl-2-phenylacetate. L(+)-tartrate salt (Compound No. 41).

The compound was prepared by using the procedure in Example 34 using (1α,5α,6α)-[3-(2-(3,4-methylenedioxyphenyl)ethyl-3-azabicyclo[3.1.0]hexyl-6-(methyl)-yl]-2-hydroxy-2-cyclopentyl-2-phenyl acetate in place of (1α,5α, 6α)-N-[3-benzyl-3-azabicyclo[3.1.0]hexyl-6-(aminomethyl)-yl]-2-hydroxy-2-cyclopentyl-2-phenylacetamide.
m.p.:88-91° C.
IR(KBr): 1725 cm$^{-1}$,1608 cm$^{-1}$.

EXAMPLE 42

Preparation of (1α,5α,6α)-[3-benzyl-3-azabicyclo[3.1.0]hexyl-6-(methyl)-yl]-2-hydroxy-2,2 diphenyl acetate. L(+)-tartrate salt (Compound No. 42)

The compound was prepared by using the method of Example 34 using (1α,5α,6α)-[3-benzyl-3-azabicyclo[3.1.0]hexyl-6-(methyl)-yl]-2-hydroxy-2,2diphenyl acetate instead of (1α,5α,6α)-N-[3-benzyl-3-azabicyclo[3.1.0]hexyl-6-(aminomethyl)-yl]-2-hydroxy-2-cyclopentyl-2-phenylacetamide.
m.p.: 53-54° C.
IR(DCM): 1730 cm$^{-1}$.

EXAMPLE 43

Preparation of (1α,5α,6α)-[3-benzyl-3-azabicyclo[3.1.0]hexyl-6-(methyl)-yl]-2-hydroxy-2-cyclohexyl-2-phenyl acetate. L(+)-tartrate salt (Compound No. 43)

The compound was prepared by using the method of Example 34 using (1α,5α,6α)-[3-benzyl-3-azabicyclo[3.1.0]hexyl-6-(methyl)-yl]-2-hydroxy-2-cyclohexyl-2-phenyl acetate instead of (1α,5α,6α)-N-[3-benzyl-3-azabicyclo[3.1.0]hexyl-6-(aminomethyl)-yl]-2-hydroxy-2-cyclopentyl-2-phenylacetamide.
m.p.: 54° C.
IR(DCM): 1725 cm$^{-1}$.

EXAMPLE 44

Preparation of (1α,5α,6α)-[3-benzyl-3-azabicyclo[3.1.0]hexyl-6-(methyl)-yl]-2-hydroxy-2-cyclopentyl-2-phenyl acetate. L(+)-tartrate salt (Compound No. 44)

The compound was prepared by using the method of Example 34 using (1α,5α,6α)-[3-benzyl-3-azabicyclo[3.1.0]hexyl-6-(methyl)-yl]-2-hydroxy-2-cyclopentyl-2-phenyl acetate instead of (1α,5α,6α)-N-[3-benzyl-3-azabicyclo[3.1.0]hexyl-6-(aminomethyl)-yl]-2-hydroxy-2-cyclopentyl-2-phenylacetamide.
m.p.: 55° C.
IR(DCM):1726 cm$^{-1}$.

EXAMPLE 45

Preparation of (1α,5α,6α)-N-[3-(3-pyridylmethyl)-3-azabicyclo[3.1.0]hexyl-6-(aminomethyl)-yl]-2-hydroxy-2-cyclohexyl-2-phenyl acetamide (Compound No. 45)

This compound was prepared following the procedure as in Example 9, Step b using 3-chloromethylpyridine hydrochloride instead of 5-(2-bromoethyl)-2,3-dihydrobenzo[2,3-b]benzofuran.
$^{1}$H-NMR (CDCl$_{3}$) δ—values: 8.49-8.47 (m, 2H, aromatic); 7.62-7.21 (m, 7H, Aromatic); 6.66 (bs, 1H), 3.56 (s, 2H), 3.07-2.30 (m, 8H), 1.76-1.21 (m, 12H).

EXAMPLE 46

Preparation of (1α,5α,6α)-N-[3-(4pyridylmethyl)-3-azabicyclo[3.1.0]hexyl-6-(aminomethyl)-yl]-2-hydroxy-2-cyclohexyl-2-phenylacetamide (Compound No. 46)

This compound was prepared following the procedure as in Example 9, Step b using 4-chloromethylpyridine hydrochloride instead of 5-(2-bromoethyl)-2,3-dihydrobenzo[2,3-b]benzofuran.
m.pt.: 61-62° C.
$^{1}$H-NMR (CDCl$_{3}$) δ—values: 8.52-8.50 (m, 2H, aromatic); 7.62-7.18 (m, 7H, Aromatic); 6.71 (bs, 1H), 3.56 (s, 2H), 3.08-2.30 (m, 7H), 1.70-1.17 (m, 13H).
IR(KBr): 1658 cm$^{-1}$

EXAMPLE 47

Preparation of (1α,5α,6α)-N-[3-(2-pyridylmethyl)-3-azabicyclo[3.1.0]hexyl-6-(aminomethyl)-yl]-2-hydroxy-2-cyclopentyl-2-phenylacetamide (Compound No. 47)

This compound was prepared following the procedure as in Example 10, Step b using 2-chloromethylpyridine hydrochloride instead of 5-(2-bromoethyl)-2,3-dihydrobenzo[2,3-b]benzofuran.
m.pt.: 62-63° C.
$^{1}$H-NMR (CDCl$_{3}$) δ—values: 8.52-8.50 (m, 2H, aromatic); 7.65-7.12 (m, 7H, Aromatic); 6.68 (bs, 1H), 3.73 (s, 2H), 3.00-2.36 (m, 8H), 1.76-1.16 (m, 12H).
IR (KBr): 1654 cm$^{-1}$

EXAMPLE 48

Preparation of (1α,5α,6α)-N-[3-(4-pyridylmethyl)-3-azabicyclo[3.1.0]hexyl-6-(aminomethyl)-yl]-2-hydroxy-2-cyclopentyl-2-phenylacetamide (Compound No. 48)

This compound was prepared following the procedure as in Example-10, Step b using 4-chloromethyl pyridinehydrochloride instead of 5-(2-bromoethyl)-2,3-dihydrobenzo[2,3-b]benzofuran.
$^{1}$H-NMR (CDCl$_{3}$) δ—values: 8.51-8.49 (m, 2H, Aromatic), 7.63-7.18 (m, 7H, aromatic), 6.64 (bs, 1H), 3.56 (s, 2H)

EXAMPLE 49

Preparation of (1α,5α,6α)-N-[3-(3-pyridylmethyl)-3-azabicyclo[3.1.0]hexyl-6-(aminomethyl)-yl]-2-hydroxy-2,2-diphenylacetamide (Compound No. 49)

The compound obtained as in Example-1 was debenzylated and then N-alkylated as given below:

Step-a: Preparation of (1α,5α,6α)-N-[3-azabicyclo[3.1.0]hexyl-6-(aminomethyl)-yl]-2-hydroxy-2,2-diphenyl acetamide:
This was synthesized using the same procedure as per Example 8, Step-a using (1α, 5α,6α)-N-3-[3-azabicyclo[3.1.0]hexyl-6-(aminomethyl)-yl]-2-hydroxy-2,2-diphenyl acetamide instead of (1α,5α,6α)-[3-benzyl-3-azabicyclo[3.1.0]hexyl-6-(methyl)-yl]-2-hydroxy-2-cyclopentyl-2-phenylacetate ¹H-NMR (CDCl₃) δ—values: 7.44-7.25 (m, 10H, Aromatic), 3.26-2.27 (m, 7H), 1.40-1.27 (m, 2H)

Step-b: To a solution of compound (1α,5α,6α)-N-[3-azabicyclo[3.1.0]-hexyl-6-(aminomethyl)-yl]-2-hydroxy-2,2-diphenylaceticamide (0.322 g, 1 mmol) in dimethyl formamide (5 ml) was added 3-chloromethylpyridine hydrochloride (0.246, 1.5 mmol) and potassium carbonate (2 mmol, 0.276 g), potassium iodide (1 mmol, 0.166 g)) and 5-(2-bromoethyl)-2,3-dihydrobenzo[2,3-b]benzofuran (0.275 gms, 1.2 mmol). The reaction mixture was stirred at RT overnight, poured into water and extracted with ethyl acetate. The combined organic layer was washed with water, brine and dried over sodium sulphate. The crude compound obtained after evaporation of the solvent under vacuum was purified by column chromatography (silica gel 100-200 mesh) eluting the compound with 20:80 ethyl acetate:hexane.

¹H-NMR (CDCl₃) δ—values: 8.51-8.50 (m, 2H, aromatic), 7.64-7.25 (m, 12H, aromatic), 6.47 (bs, 1H), 3.61 (s, 2H), 3.23-3.18 (m, 2H), 2.96-2.88 (m, 2H), 2.10-2.03 (m, 2H), 1.48-1.14 (m, 3H).

IR (DCM): 1646 cm⁻¹

EXAMPLE 50

Preparation of (1α,5α,6α)-N-[3-(4-pyridylmethyl)-3-azabicyclo[3.1.0]hexyl-6-(aminomethyl)-yl]-2-hydroxy-2,2-diphenyl acetamide (Compound No. 50)

This compound was prepared following the procedure as in Example 49, Step b using 4-chloromethyl pyridine hydrochloride instead of 3-chloromethyl pyridine hydrochloride.

¹H-NMR (CDCl₃) δ—values: 8.48-8.46 (m, 2H, Aromatic), 7.66-7.18 (m, 12H, Aromatic), 6.52 (bs, 1H), 3.57 (s, 2H), 3.20-3.16 (m, 2H), 2.96-2.93 (m, 2H), 2.35-2.30 (m, 2H), 1.60-1.25 (m, 3H).

IR (KBr): 1658 cm⁻¹

EXAMPLE 51

Preparation of (1α,5α,6α)-N-[3-(2-pyridylmethyl)-3-azabicyclo[3.1.0]hexyl-6-(aminomethyl)-yl]-2-hydroxy-2,2-diphenyl acetamide (Compound No. 51)

A solution of (1α,5α,6α)-N-[3-azabicyclo[3.1.0]hexyl-6-(aminomethyl)-yl]-2-hydroxy-2,2-diphenylacetamide (0.322 g, 1 mmol), 2-pyridine carboxaldehyde (0.256 g, 2.4 mmol), sodium triacetoxy borohydride (0.678 g, 3.2 mmol) and acetic acid (0.228 g, 3.8 mmols) in tetrahydrofuran (25 ml) was stirred for 4 days. The reaction mixture was poured into saturated sodium bicarbonate solution and extracted with ethyl acetate. The organic layer was washed with water, dried over sodium sulphate and concentrated under reduced pressure. The residue was purified by column chromatography (100×200 mesh, size silicagel) using 80:20 ethyl acetate: dichloromethane.

¹H-NMR (CDCl₃) δ—values: 8.53-8.52 (m, 1H, Aromatic), 7.67-7.14 (m, 13H, Aromatic), 6.39 (bs, 1H), 3.74 (s, 2H), 3.20-3.16 (m, 2H), 3.01-2.98 (m, 2H), 2.15-2.02 (m, 3H), 1.33-1.19 (m, 2H)

IR(KBr): 1658 cm⁻¹

EXAMPLE 52

Preparation of (1α,5α,6α)-N-[3-(2-pyridylmethyl)-3-azabicyclo[3.1.0]hexyl-6-(aminomethyl)-yl]-2-hydroxy-2-cyclopentyl-2-phenyl acetamide (Compound No. 52)

This compound was synthesized following the procedure of Example 51 using (1α,5α,6α)-N-[3-azabicyclo[3.1.0]hexyl-6-(aminomethyl)-yl]-2-hydroxy-2-cyclopentyl-2-phenyl acetamide instead of (1α,5α,6α)-N-[3-azabicyclo[3.1.0]hexyl-6-(aminomethyl)-yl]-2-hydroxy-2,2-diphenyl acetamide.

¹H-NMR (CDCl₃) δ—values: 8.52 (m, 1H, Aromatic), 7.67-7.16 (m, 8H, Aromatic), 6.47 (bs, 1H), 3.74 (s, 2H), 3.08-2.02 (m, 9H), 1.66-0.88 (m, 10H)

IR (KBr): 1644 cm⁻¹

EXAMPLE 53

Preparation of (1α,5α,6α)-N-[3-(3-pyridylmethyl)-3-azabicyclo[3.1.0]hexyl-6-(aminomethyl)-yl]-2-hydroxy-2-cyclopentyl-2-phenyl acetamide (Compound No. 53)

This compound was synthesized using the procedure of Example 10, Step b but using 3-chloromethylpyridine hydrochloride instead of 5-(2-bromoethyl)-2,3-dihydrobenzo[2,3-b) benzofuran.

¹H-NMR (CDCl₃) δ—values: 8.53-8.51 (m, 2H, Aromatic), 7.63-7.18 (m, 7H, Aromatic), 6.5 (bs, 1H), 3.57 (s, 2H), 3.12-3.91 (m, 6H), 2.33-2.31 (m, 2H), 1.40-1.17 (m, 10H)

IR (KBr): 1642 cm⁻¹

EXAMPLE 54

Preparation of (1α,5α,6α)-N-[3-(3-methyl-2-butenyl)-3-azabicyclo[3.1.0]hexyl-6-(aminomethyl)-yl]-2-hydroxy-2-cyclopentyl-2-phenyl acetamide (Compound No. 54)

This compound was synthesized by following the procedure of Example 10, Step b but using 1-bromo-3-methyl-but-2-ene instead of 5-(2-bromoethyl)-2,3-dihydrobenzo[2,3-b] benzofuran.

¹H-NMR (CDCl₃) δ—values: 7.61-7.26 (m, 5H, Aromatic), 6.43 (bs, 1H), 5.20 (t, 1H), 3.07-2.98 (m, 7H), 2.33-2.30 (m, 2H), 1.76-0.92 (m, 17H)

EXAMPLE 55

Preparation of (1α,5α,6α)-N-[3-(3,4-methylenedioxyphenyl)methyl-3-azabicyclo[3.1.0]hexyl-6-(aminomethyl)-yl]-2-hydroxy-2-cyclopentyl-2-phenylacetamide (Compound No. 55)

This compound was synthesized by following the procedure of Example 51 but using 3,4-methylenedioxybenzaldehyde instead of 2-pyridine carboxaldehyde, and (1α,5α,6α)-N-[3-azabicyclo[3.1.0]hexyl-6-(aminomethyl)-yl]-2-hydroxy-2,2-diphenyl acetamide instead of (1α,5α,6α)-N-[3-azabicyclo[3.1.0]hexyl-6-(aminomethyl)-yl]-2-hydroxy-2,2-diphenylacetamide.

m.p.: 148-150° C.

¹H-NMR (CDCl₃) δ—values: 7.61-6.66 (m, 8H, Aromatic), 6.42 (bs, 1H), 5.93 (s, 2H), 3.46 (s, 2H), 3.19-2.88 (m, 6H), 2.29-2.27 (m, 2H), 1.71-1.22 (m, 11H)
IR (KBr): 1652 cm⁻¹

EXAMPLE 56

Preparation of (1α,5α,6α)-N-[3-(3,4-methylenedioxyphenyl)methyl-3-azabicyclo[3.1.0]hexyl-6-(aminomethyl)-yl]-2-hydroxy-2-cyclohexyl-2-phenyl acetamide (Compound No. 56)

This compound was synthesized by following the procedure of Example 51 but using (1α,5α,6α)-N-[3-azabicyclo[3.1.0]hexyl-6-(aminomethyl)-yl]-2-hydroxy-2-cyclohexyl-2-phenylacetamide instead of (1α,5α,6α)-N-[3-azabicyclo[3.1.0]hexyl-6-(aminomethyl)-yl]-2-hydroxy-2,2-diphenylacetamide and 3,4-methylenedioxybenzaldehyde instead of 2-pyridine carboxaldehyde.
m.p.: 130-133° C.
¹H-NMR (CDCl₃) δ—values: 7.61-6.68 (m, 8H) 5.93 (s, 2H), 3.45 (s, 2H), 2.92-2.84 (m, 5H), 2.28-2.26 (m, 2H), 1.34-1.17 (m, 13H)
IR (KBr): 1651 cm⁻¹

EXAMPLE 57

Preparation of (1α,5α,6α)-[3-(4-methyl-3-pentenyl)-3-azabicyclo[3.1.0]hexyl-6-(methyl)-yl]-2-hydroxy-2-cyclohexyl-2-phenyl acetate. L(+) tartrate salt (Compound No. 57)

This compound was synthesized by following the procedure of Example 34 but using (1α,5α,6α)-[3-(4-methyl-3-pentenyl)-3-azabicyclo[3.1.0]hexyl-6-(methyl)-yl]-2-hydroxy-2-cyclohexyl-2-phenyl acetate instead of (1α,5α,6α)-N-[3-benzyl-3-azabicyclo[3.1.0]hexyl-6(aminomethyl)-yl]-2-hydroxy-2-cyclopentyl-2-phenyl acetamide.
m.p.: 87-89° C.
HPLC: 94.6%

EXAMPLE 58

Preparation of (1α,5α,6α)-[3-(2-3,4-methylenedioxyphenyl)ethyl)-3-azabicyclo[3.1.0]hexyl-6-(methyl)-yl]-2-hydroxy-2-cyclohexyl-2-phenyl acetate. L(+) tartrate salt (Compound No. 58)

This compound was synthesized by following the procedure of Example 34 but using (1α,5α,6α)-[3-(2-(3,4-methylenedioxyphenyl)ethyl)-3-azabicyclo[3.1.0]hexyl-6-(methyl)-yl]-2-hydroxy-2-cyclohexyl-2-phenyl acetate instead of (1α,5α,6α)-N-[3-benzyl-3-azabicyclo[3.1.0]hexyl-6(aminomethyl)-yl]-2-hydroxy-2-cyclopentyl-2-phenyl acetamide.
m.p.: 76° C. (starts decomposing)
HPLC: 97.48%

EXAMPLE 59

Preparation of (1α,5α,6α)-[3-(1-phenylethyl)-3-azabicyclo[3.1.0]hexyl-6-(methyl)-yl]-2-hydroxy-2-cyclopentyl-2-phenyl acetate. L(+) tartrate salt (Compound No. 59)

This compound was synthesised following the procedure of Example 34 but using (1α,5α,6α)-[3-(1-phenylethyl)-3-azabicyclo[3.1.0]hexyl-6-methyl)-yl]-2-hydroxy-2-cyclopentyl-2-phenyl acetate instead of (1α,5α,6α)-N-[3-benzyl-3-azabicyclo[3.1.0]hexyl-6(aminomethyl)-yl]-2-hydroxy-2-cyclopentyl-2-phenyl acetamide.
m.p.: 78° C. (starts decomposing)
HPLC:94.2%

EXAMPLE-60

Preparation of (1α,5α,6α)-N-[3-benzyl-3-azabicyclo[3.1.0]-hexyl-6-(aminomethyl)-yl]-2-hydroxy-2-cyclopentyl-2-phenyl acetamide hydrochloride salt (Compound No. 60)

This compound was synthesized by the following procedure:
Ethereal hydrochloric acid (10 ml) was added to a solution of compound 3 (1 mmol) in ethanol (5 ml). The reaction mixture was stirred at room temperature and then concentrated under reduced pressure.
HPLC:96.39%

EXAMPLE 61

Preparation of (1α,5α,6α)-N-[3-benzyl-3-azabicyclo[3.1.0]-hexyl-6-(aminomethyl)-yl]-2-hydroxy-2-cyclopentyl-2-phenyl acetamide. L(−) malic acid salt (Compound No. 61)

This compound was synthesised by following the procedure of Example 34 but using L(−) malic acid instead of L-(+) tartaric acid
HPLC:98.28%

EXAMPLE 62

Preparation of (1α,5α,6α)-N-[3-benzyl-3-azabicyclo[3.1.0]-hexyl-6-(aminomethyl)-yl]-2-hydroxy-2-cyclopentyl-2-phenyl acetamide. Maleate salt (Compound No. 62)

This compound was synthesized by following the procedure of Example 34 but using malic acid instead of L-(+) tartaric acid
HPLC:98.37%

Biological Activity

Radioligand Binding Assays:
The affinity of test compounds for $M_2$ and $M_3$ muscarinic receptor subtypes was determined by [³H]-N-methylscopolamine binding studies using rat heart and submandibular gland respectively as described by Moriya et al., (Life Sci, 1999, 64 (25):2351-2358) with minor modifications.

Membrane preparation: Submandibular glands and heart were isolated and placed in ice cold homogenising buffer (HEPES 20 mM, 10 mM EDTA, pH 7.4) immediately after sacrifice. The tissues were homogenised in 10 volumes of homogenising buffer and the homogenate was filtered through two layers of wet gauze and filtrate was centrifuged at 500 g for 10 min. The supernatant was subsequently centriged at 40,000 g for 20 min. The pellet thus obtained was resuspended in same volume of assay buffer (HEPES 20 mM, EDTA 5 mM, pH 7.4) and were stored at −70° C. until the time of assay.

Ligand binding assay: The compounds were dissolved and diluted in DMSO. The membrane homogenates (150-250 μg protein) were incubated in 250 μl of assay buffer (HEPES 20 mM, pH 7.4) at 24-25° C. for 3 h. Non-specific binding was determined in the presence of 1 µM atropine. The incubation was terminated by vacuum filtration over GF/B fiber filters (Wallac). The filters were then washed with ice cold 50 mM Tris HCl buffer (pH 7.4). The filter mats were dried and bound radioactivity retained on filters was counted. The $IC_{50}$ & Kd were estimated by using the non-linear curve fitting program using G Pad Prism software. The value of inhibition constant Ki was calculated from competitive binding studies by using Cheng & Prusoff equation (*Biochem Pharmacol*, 1973, 22: 3099-3108), $Ki=IC_{50}/(1+L/Kd)$, where L is the concentration of [$^3$H]NMS used in the particular experiment.

Functional Experiments using Isolated Rat Bladder:

Methodology:

Animals were euthanized by overdose of urethane and whole bladder was isolated and removed rapidly and placed in ice cold Tyrode buffer with the following composition (mMol/L) NaCl 137; KCl 2.7; $CaCl_2$ 1.8; $MgCl_2$ 0.1; $NaHCO_3$ 11.9; $NaH_2PO_4$ 0.4; Glucose 5.55 and continuously gassed with 95% $O_2$ and 5% $CO_2$.

The bladder was cut into longitudinal strips (3 mm wide and 5-6 mm long) and mounted in 10 ml organ baths at 30° C., with one end connected to the base of the tissue holder and the other end connected to a polygraph through a force displacement transducer. Each tissue was maintained at a constant basal tension of 2 g and allowed to equilibrate for 1 hour during which the PSS was changed every 15 min. At the end of equilibration period the stabilization of the tissue contractile response was assessed with 1 µmol/L of Carbachol consecutively for 2-3 times. Subsequently a cumulative concentration response curve to carbachol ($10^{-9}$ mol/L to $3\times10^{-5}$ mol/L) was obtained. After several washes, once the baseline was achieved, cumulative concentration response curve was obtained in presence of NCE (NCE added 20 min. prior to the second CRC).

The contractile results were expressed as % of control E max. ED50 values were calculated by fitting a non-linear regression curve (Graph Pad Prism). pKB values were calculated by the formula pKB=−log[(molar concentration of antagonist/(dose ratio−1))]

where, dose ratio=ED50 in the presence of antagonist/ED50 in the absence of antagonist.

In Vivo Experiments Using Anaesthetized Rabbit

Methodology

Male rabbits were anaesthetized with urethane 1.5 g/kg intravenously. Trachea was cannulated to maintain the patency of airway. Femoral vein and femoral arteries of both sides were cannulated for the administration of vehicle or drug substances for the measurement of BP and administration of carbachol intra-arterially respectively.

Polyethylene tubing was introduced into the bladder through the urethra and tied at the neck of the bladder. The other end of the catheter was connected to the Grass polygraph through a Statham pressure transducer. The bladder was filled with warm (37° C.) saline. Both the ureters were ligated and cut proximally to drain the urine coming from kidneys. A stabilization period of 30-60 was allowed for stabilization of parameters from surgical procedures.

Salivary response was assessed by measuring the weight of a preweighted cotton gauze kept for 2 minutes in the buccal cavity immediately after the carbachol challenge.

At the end of stabilization period 2 control responses to carbachol (1.5 µg/kg intra-arterial) on bladder pressure and salivation were obtained and this response was considered as 100%. Subsequently, the effect of increasing dose of NCE (ranging from 3 µg/kg to 1 mg/kg) or vehicle (i.v., 15 min before carbachol challenge) was examined.

The change in bladder pressure and salivation were expressed as % change from pretreatment control averages. The $ID_{50}$ values for salivation and bladder pressure inhibition were calculated using Graph Pad Prism software, by fitting the values at dose into non-linear regression curve. Oxybutynin and Tolterodine were used as standards for comparison.

The bladder selectivity to salivation was calculated by using following formula and expressed as fold of selectivity of oxybutinin in the same model.

$$\frac{ID_{50} \text{ Salivary response}}{ID_{50} \text{ Bladder pressure}}$$

The results of the in-vitro and in-vivo tests are listed in Tables II and III.

In-Vitro Tests

TABLE II

| | Receptor Binding Assay | | | Functional |
|---|---|---|---|---|
| | $M_2$ pKi | $M_3$ pKi | Selectivity $M_2/M_3$ | Assay $pK_B$ |
| Compound No. 1 | 6.59 | 7.6 | 10 | 8.14 |
| Compound No. 2 | 6.85 | 8.25 | 25 | 8.7 |
| Compound No. 3 | 7.02 | 8.23 | 16 | 8.6 |
| Compound No. 4 | 8.6 | 9.41 | 6 | 8.79 |
| Compound No. 5 | 8.4 | 8.91 | 3 | 7.4 |
| Compound No. 6 | 8.46 | 9.25 | 6 | 8.5 |
| Compound No. 7 | 7.9 | 8.23 | 2 | 7.88 |
| Compound No. 8 | 7.87 | 8.05 | 15 | |
| Compound No. 9 | 6.59 | 7.41 | 6.6 | 6.77 |
| Compound No. 10 | 6.47 | 7.49 | 10.47 | 7.87 |
| Compound No. 11 | 8.03 | 8.62 | 3.89 | 8.40 |
| Compound No. 12 | 7.64 | 8.38 | 5.49 | 8.42 |
| Compound No. 13 | 6.48 | 7.28 | 6.3 | 7.21 |
| Compound No. 14 | 5.7 | 6.72 | 10.5 | |
| Compound No. 15 | 6.59 | 7.87 | 19 | 7.81 |
| Compound No. 16 | 6.75 | 7.63 | 7.6 | 7.94 |
| Compound No. 17 | 8.36 | 9.1 | 5.5 | 8.09 |
| Compound No. 18 | 8.4 | 9.15 | 5.6 | 7.4 |
| Compound No. 19 | 8.15 | 8.8 | 4.5 | 7.99 |
| Compound No. 20 | 7.9 | 8.73 | 6.8 | 7.1 |
| Compound No. 21 | 6.59 | 7.82 | 17 | 7.5 |
| Compound No. 22 | 7.06 | 8.23 | 14.8 | 7.65 |
| Compound No. 23 | 6.23 | 6.8 | 3.7 | |
| Compound No. 24 | 6.56 | 7.51 | 8.9 | 7.54 |
| Compound No. 25 | 6.37 | 7.6 | 17 | 7.9 |
| Compound No. 26 | 9.52 | 9.5 | 0.95 | 7.94 |
| Compound No. 27 | 9.65 | 9.85 | 1.6 | 8.27 |
| Compound No. 28 | 7.85 | 8.4 | 3.5 | 8.5 |
| Compound No. 29 | 7.91 | 8.96 | 11.2 | 9.15 |
| Compound No. 30 | 9.13 | 9.46 | 2 | 8.79 |
| Compound No. 31 | 9.15 | 9.75 | 3.98 | 8.37 |
| Compound No. 32 | 6.2 | 7.65 | 28 | 7.8 |
| Compound No. 33 | 7.39 | 8.4 | 10.23 | |
| Compound No. 34 | 7.22 | 8.23 | 8 | 8.8 |
| Compound No. 35 | 7.35 | 8.46 | 13 | 9.21 |
| Compound No. 36 | 6.21 | 7.65 | | 7.8 |
| Compound No. 37 | 7.24 | 8.23 | 8 | |
| Compound No. 38 | 6.37 | 7.19 | 6.6 | |
| Compound No. 39 | 7.79 | 8.36 | 3.7 | |
| Compound No. 40 | 9.08 | 9.36 | 1.9 | |
| Compound No. 41 | 8.1 | 8.23 | 1.25 | 8.35 |
| Compound No. 42 | 8.63 | 9.3 | 4.64 | 8.46 |
| Compound No. 43 | 8.15 | 8.46 | 2.02 | 7.7 |
| Compound No. 44 | 8.63 | 9.16 | 3.7 | 7.81 |

TABLE II-continued

| | Receptor Binding Assay | | | Functional |
| --- | --- | --- | --- | --- |
| | $M_2$ pKi | $M_3$ pKi | Selectivity $M_2/M_3$ | Assay $pK_B$ |
| Compound No. 45 | <6 | 6.63 | | |
| Compound No. 46 | <6 | 7.17 | | |
| Compound No. 47 | 6.15 | 7.42 | | |
| Compound No. 48 | <6 | 7.14 | | |
| Compound No. 49 | <6 | 7.16 | | |
| Compound No. 50 | <6 | 6.94 | | |
| Compound No. 57 | 8.46 | 9.34 | | 7.5 |
| Compound No. 58 | 7.82 | 8.3 | | 7.55 |
| Compound No. 60 | 7.31 | 8.28 | | 8.38 |
| Compound No. 61 | 7.36 | 8.29 | | 8.66 |
| Compound No. 62 | 7.28 | 8.17 | | 8.94 |
| Tolterodine | 8.4 | 8.3 | 0.98 | 9.05 |
| Oxybutynin | 8.3 | 9.2 | 7.34 | 8.93 |
| Atropine | 9 | 9.6 | 0.83 | 9.96 |

In-Vivo Tests

TABLE III

| Compound | $IC_{50}$ Bladder Pressure | $IC_{50}$ Salivary Response | Fold Selectivity | Fold of Oxybutynin |
| --- | --- | --- | --- | --- |
| Oxybutynin | 36.6 ± 12 | 21.6 + 5 | 0.58 + 0 | 1.0 |
| Tolterodine | 26.9 + 4 | 35.1 + 9 | 1.76 + 0 | 2.31 |
| Compound No. 42 | 20.13 + 2 | 15.41 + 1 | 0.80 + 0 | 1.38 |
| Compound No. 43 | 53.81 + 2 | 85.06 + 28 | 1.94 + 0 | 3.34 |
| Compound No. 44 | 23.25 + 6 | 18.62 + 4 | 1.09 + 0 | 1.88 |
| Compound No. 35 | 15.84 | 31.62 | — | 3.45 |
| Compound No. 36 | 398.1 | 501.2 | — | 2.17 |

While the present invention has been described in terms of its specific embodiments, certain modifications and equivalents will be apparent to those skilled in the art and are intended to be included within the scope of the present invention.

We claim:

1. A compound having the structure of Formula I:

FORMULA-I

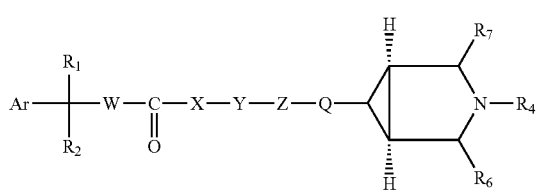

and its pharmaceutically acceptable salts, pharmaceutically acceptable enantiomers, diastereomers, or N-oxides, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) amino or N-lower alkyl($C_1$-$C_4$) amino carbonyl;

$R_1$ represents a hydrogen, hydroxy, hydroxy methyl, amino, alkoxy, carbamoyl or halogen (e.g. fluorine, chlorine, bromine and iodine);

$R_2$ represents alkyl, $C_3$-$C_7$ cycloalkyl ring, a $C_3$-$C_7$ cyclo alkenyl ring, an aryl or a heteroaryl ring having 1 to 2 hetero atoms selected from a group consisting of oxygen, sulphur and nitrogen atoms; the aryl or a heteroaryl ring may be unsubstituted or substituted by one to three substituents independently selected from lower alkyl ($C_1$-$C_4$), lower perhalo alkyl ($C_1$-$C_4$), cyano, hydroxy, nitro, lower alkoxycarbonyl, halogen, lower alkoxy ($C_1$-$C_4$), lower perhalo alkoxy ($C_1$-$C_4$), unsubstituted amino, N-lower alkylamino ($C_1$-$C_4$), N-lower alkylamino carbonyl ($C_1$-$C_4$);

W represents $(CH_2)_p$, where p represents 0 to 1;

X represents an oxygen, sulphur, nitrogen or no atom;

Y represents $CHR_5CO$ wherein $R_5$ represents hydrogen or methyl or $(CH_2)_q$ wherein q represents 0 to 4;

Z represents oxygen, sulphur, $NR_{10}$, wherein $R_{10}$ represents hydrogen, $C_{1-6}$ alkyl;

Q represents $(CH_2)_n$ wherein n represents 0 to 4, or $CHR_8$ wherein $R_8$ represents H, OH, $C_{1-6}$, alkyl, alkenyl alkoxy or $CH_2CHR_9$ wherein $R_9$ represents H, OH, lower alkyl ($C_1$-$C_4$) or lower alkoxy ($C_1$-$C_4$);

$R_6$ and $R_7$ are independently selected from COOH, H, $CH_3$, $CONH_2$, $NH_2$, $CH_2NH_2$;

$R_4$ represents $C_1$-$C_{15}$ saturated or unsaturated aliphatic hydrocarbon groups in which any 1 to 6 hydrogen atoms may be substituted with the group independently selected from halogen, arylalkyl, arylalkenyl, heteroarylalkyl or heteroarylalkenyl having 1 to 2 hetero atoms selected from a group consisting of nitrogen, oxygen and sulphur atoms with option that any 1 to 3 hydrogen atoms on the ring in said arylalkyl, arylalkenyl, heteroarylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkyl($C_1$-$C_4$) amino, N-lower alkyl ($C_1$-$C_4$) amino carbonyl.

2. The compound according to claim 1 having the structure of Formula II (Formula I when $R_6$ and $R_7$=H) and its pharmaceutically acceptable salts, pharmaceutically acceptable enantiomers, diastereomers, or N-oxides, wherein Ar, $R_1$, $R_2$, W, X, Y, Z, Q and $R_4$ are as defined for Formula I

FORMULA-II

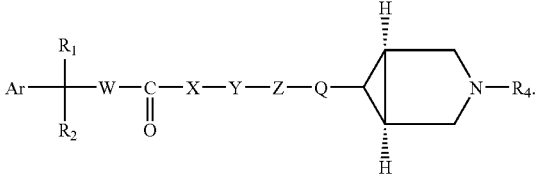

3. The compound according to claim 1 having the structure of Formula III (Formula I wherein W is $(CH_2)p$ where p=0, X is no atom and Y is $(CH_2)q$ where q=0, $R_6$=H, $R_7$=H) and $R_2$ its pharmaceutically acceptable salts, pharmaceutically acceptable enantiomers, diastereomers, or N-oxides, wherein Ar, $R_1$, $R_2$, Z, Q and $R_4$ are as defined for Formula I

FORMULA-III

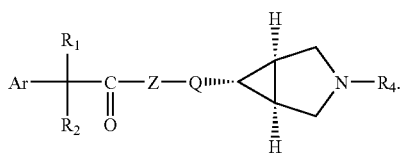

4. The compound according to claim 1 having the structure of Formula IV [Formula I wherein W is (CH$_2$)p where p=0, X is no atom and Y is (CH$_2$)q where q=0, R$_6$=H, R$_7$=H and

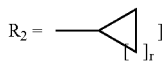

and its pharmaceutically acceptable salts, pharmaceutically acceptable enantiomers, diastereomers, or N-oxides, wherein Ar, R$_1$, Z, Q and R$_4$ are as defined for Formula I, and r is 1 to 4

Formula IV

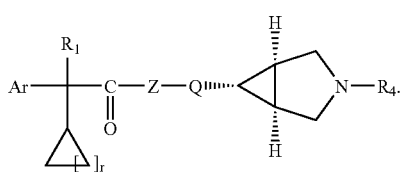

5. The compound according to claim 1 having the structure of Formula V (Formula-I wherein W is (CH$_2$)p where p=0, X is no atom and Y is (CH$_2$)q where q=0, R$_6$=H, R$_7$=H,

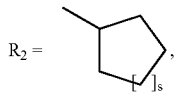

R$_1$ is hydroxy, Ar is phenyl), and its pharmaceutically acceptable salts, esters, enantiomers, or N-oxides, wherein R$_4$, Z and Q are the same as defined for Formula I, and s represents 1 to 2

Formula V

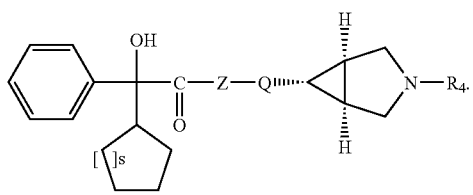

6. A compound selected from the group consisting of:
(1α,5α,6α)-N-[3-benzyl-3-azabicyclo[3.1.0]hexyl-6-(aminomethyl)-yl]-2-hydroxy-2,2-diphenyl acetamide (Compound No. 1);
(1α,5α,6α)-N-[3-benzyl-3-azabicyclo[3.1.0]hexyl-6-(aminomethyl)-yl]-2-hydroxy-2-cyclohexyl-2-phenyl acetamide (Compound No. 2);
(1α,5α,6α)-N-[3-benzyl-3-azabicyclo[3.1.0]hexyl-6-(aminomethyl)-yl]-2-hydroxy-2-cyclopentyl-2-phenyl acetamide (Compound No. 3);
(1α,5α,6α)-[3-benzyl-3-azabicyclo[3.1.0]hexyl-6-(methyl)-yl]-2-hydroxy-2,2-diphenyl acetate (Compound No. 4);
(1α,5α,6α)-[3-benzyl-3-azabicyclo[3.1.0]hexyl-6-(methyl)-yl]-2-hydroxy-2-cyclohexyl-2-phenyl acetate (Compound No. 5);
(1α,5α,6α)-[3-benzyl-3-azabicyclo[3.1.0]hexyl-6-(methyl)-yl]-2-hydroxy-2-cyclopentyl-2-phenyl acetate (Compound No. 6);
(1α,5α,6α)-[3-(2-(2,3-dihydrobenzofuran-5-yl)ethyl)-3-azabicyclo[3.1.0]hexyl-6-(methyl)-yl]-2-hydroxy-2-cyclohexyl-2-phenyl acetate (Compound No. 7);
(1α,5α,6α)-[3-(2-(2,3-dihydrobenzofuran-5-yl)ethyl)-3-azabicyclo[3.1.0]hexyl-6-(methyl)-yl]-2-hydroxy-2-cyclopentyl-2-phenyl acetate (Compound No. 8);
(1α,5α,6α)-N-[3-(2-(2,3-dihydrobenzofuran-5-yl)ethyl)-3-azabicyclo[3.1.0]hexyl-6-(aminomethyl)-yl]-2-hydroxy-2-cyclohexyl-2-phenyl acetamide (Compound No. 9);
(1α,5α,6α)-N-[3-(2-(2,3-dihydrobenzofuran-5-yl)ethyl)-3-azabicyclo[3.1.0]hexyl-6-(aminomethyl)-yl]-2-hydroxy-2-cyclopentyl-2-phenyl acetamide (Compound No. 10);
(1α,5α,6α)-[3-(2-(3,4-methylenedioxyphenyl)ethyl)-3-azabicyclo[3.1.0]hexyl-6-(methyl)-yl]-2-hydroxy-2-cyclopentyl-2-phenyl acetate (Compound No. 11);
(1α,5α,6α)-[3-(2-(3,4-methylenedioxyphenyl)ethyl)-3-azabicyclo[3.1.0]hexyl-6-(methyl)-yl]-2-hydroxy-2-cyclohexyl-2-phenyl acetate (Compound No. 12);
(1α,5α,6α)-N-[3-(2-(3,4-methylenedioxyphenyl)ethyl)-3-azabicyclo[3.1.0]hexyl-6-(aminomethyl)-yl]-2-hydroxy-2-cyclopentyl-2-phenyl acetamide (Compound No. 13);
(1α,5α,6α)-N-[3-(2-(3,4-methylenedioxyphenyl)ethyl)-3-azabicyclo[3.1.0]hexyl-6-(aminomethyl)-yl]-2-hydroxy-2-cyclohexyl-2-phenyl acetamide (Compound No. 14);
(1α,5α,6α)-N-[3-(4-methyl-3-pentenyl)-3-azabicyclo[3.1.0]hexyl-6-(aminomethyl)-yl]-2-hydroxy-2-cyclohexyl-2-phenyl acetamide (Compound No. 15);
(1α,5α,6α)-N-[3-(4-methyl-3-pentenyl)-3-azabicyclo[3.1.0]hexyl-6-(aminomethyl)-yl]-2-hydroxy-2-cyclopentyl-2-phenyl acetamide (Compound No. 16);
(1α,5α,6α)-[3-(4-methyl-3-pentenyl)-3-azabicyclo[3.1.0]hexyl-6-(methyl)-yl]-2-hydroxy-2-cyclohexyl-2-phenyl acetate (Compound No. 17);
(1α,5α,6α)-[3-(4-methyl-3-pentenyl)-3-azabicyclo[3.1.0]hexyl-6-(methyl)-yl]-2-hydroxy-2-cyclopentyl-2-phenyl acetate (Compound No. 18);
(1α,5α,6α)-[3-(1-phenylethyl)-3-azabicyclo[3.1.0]hexyl-6-(methyl)-yl]-2-hydroxy-2-cyclopentyl-2-phenyl acetate (Compound No. 19);
(1α,5α,6α)-[3-(1-phenylethyl)-3-azabicyclo[3.1.0]hexyl-6-(methyl)-yl]-2-hydroxy-2-cyclohexyl-2-phenyl acetate (Compound No. 20);
(1α,5α,6α)-N-[3-(1-phenylethyl)-3-azabicyclo[3.1.0]hexyl-6-(aminomethyl)-yl]-2-hydroxy-2-cyclohexyl-2-phenyl acetamide (Compound No. 21);
(1α,5α,6α)-N-[3-(1-phenylethyl)-3-azabicyclo[3.1.0]hexyl-6-(aminomethyl)-yl]-2-hydroxy-2-cyclopentyl-2-phenyl acetamide (Compound No. 22);
(1α,5α,6α)-N-[3-benzyl-3-azabicyclo[3.1.0]hexyl-6-(1-aminoethyl)-yl]-2-hydroxy-2,2-diphenyl acetamide (Compound No. 23);

(1α,5α,6α)-N-[3-benzyl-3-azabicyclo[3.1.0]hexyl-6-(1-aminoethyl)-yl]-2-hydroxy-2-cyclohexyl-2-phenyl acetamide (Compound No. 24);

(1α,5α,6α)-N-[3-benzyl-3-azabicyclo[3.1.0]hexyl-6-(1-aminoethyl)-yl]-2-hydroxy-2-cyclopentyl-2-phenyl acetamide (Compound No. 25);

(1α,5α,6α)-[3-(3-methyl-2-butenyl)-3-azabicyclo[3.1.0]hexyl-6-(methyl)-yl]-2-hydroxy-2-cyclohexyl-2-phenyl acetate (Compound No. 26);

(1α,5α,6α)-[3-(3-methyl-2-butenyl)-3-azabicyclo[3.1.0]hexyl-6-(methyl)-yl]-2-hydroxy-2-cyclopentyl-2-phenyl acetate (Compound No. 27);

(2R)-(+)-(1α,5α,6α)-N-[3-benzyl-3-azabicyclo[3.1.0]hexyl-6-(aminomethyl)-yl]-2-hydroxy-2-cyclohexyl-2-phenyl acetamide (Compound No. 28);

(2R)-(+)-(1α,5α,6α)-N-[3-benzyl-3-azabicyclo[3.1.0]hexyl-6-(aminomethyl)-yl]-2-hydroxy-2-cyclopentyl-2-phenyl acetamide (Compound No. 29);

(2R)(+)-(1α,5α,6α)-[3-benzyl-3-azabicyclo[3.1.0]hexyl-6-(methyl)-yl]-2-hydroxy-2-cyclohexyl-2-phenyl acetate (Compound No. 30);

(2R)(+)-(1α,5α,6α)-[3-benzyl-3-azabicyclo[3.1.0]hexyl-6-(methyl)-yl]-2-hydroxy-2-cyclopentyl-2-phenyl acetate (Compound No. 31);

(2S)-(−)-(1α,5α,6α)-N-[3-benzyl-3-azabicyclo[3.1.0]hexyl-6-(aminomethyl)-yl]-2-hydroxy-2-cyclopentyl-2-phenyl acetamide (Compound No. 32);

(2S)-(−)-(1α,5α,6α)-[3-benzyl-3-azabicyclo[3.1.0]hexyl-6-(methyl)-yl]-2-hydroxy-2-cyclopentyl-2-phenyl acetate (Compound No. 33);

(1α,5α,6α)-N-[3-benzyl-3-azabicyclo[3.1.0]hexyl-6-(aminomethyl)-yl]-2-hydroxy-2-cyclopentyl-2-phenyl acetamide L-(+)-tartrate salt (Compound No. 34);

(2S)-(−)-(1α,5α,6α)-N-[3-benzyl-3-azabicyclo[3.1.0]hexyl-6-(aminomethyl)-yl]-2-hydroxy-2-cyclopentyl-2-phenyl acetamide L-(+)-tartrate salt (Compound No. 35);

(2R)-(+)-(1α,5α,6α)-N-[3-benzyl-3-azabicyclo[3.1.0]hexyl-6-(aminomethyl)-yl]-2-hydroxy-2-cyclopentyl-2-phenyl acetamide L-(+)-tartrate salt (Compound No. 36);

(1α,5α,6α)-N-[3-benzyl-3-azabicyclo[3.1.0]hexyl-6-(aminomethyl)-yl]-2-hydroxy-2-cyclobutyl-2-phenyl acetamide (Compound No. 37);

(1α,5α,6α)-N-[3-benzyl-3-azabicyclo[3.1.0]hexyl-6-(aminomethyl)-yl]-2-hydroxy-2-cyclopropyl-2-phenyl acetamide (Compound No. 38);

(1α,5α,6α)-N-[3-(3-methyl-2-butenyl)-3-azabicyclo[3.1.0]hexyl-6-(aminomethyl)-yl]-2-hydroxy-2-cyclohexyl-2-phenyl acetamide (Compound No. 39);

(1α,5α,6α)-[3-(3,4-methylenedioxyphenyl)methyl-3-azabicyclo[3.1.0]hexyl-6-(methyl)-yl]-2-hydroxy-2-cyclopentyl-2-phenyl acetate (Compound No. 40);

(1α,5α,6α)-[3-(2-(3,4-methylenedioxyphenyl)ethyl)-3-azabicyclo[3.1.0]hexyl-6-(methyl)-yl]-2-hydroxy-2-cyclopentyl-2-phenyl acetate L-(+)-tartrate salt (Compound No. 41);

(1α,5α,6α)-[3-benzyl-3-azabicyclo[3.1.0]hexyl-6-(methyl)-yl]-2-hydroxy-2,2diphenyl acetate L(+)-tartrate salt (Compound No. 42);

(1α,5α,6α)-[3-benzyl-3-azabicyclo[3.1.0]hexyl-6-(methyl)-yl]-2-hydroxy-2-cyclohexyl-2-phenyl acetate L(+)-tartrate salt (Compound No. 43);

(1α,5α,6α)-[3-benzyl-3-azabicyclo[3.1.0]hexyl-6-(methyl)-yl]-2-hydroxy-2-cyclopentyl-2-phenyl acetate L(+)-tartrate salt (Compound No. 44);

(1α,5α,6α)-N-[3-(3-pyridylmethyl)-3-azabicyclo[3.1.0]hexyl-6-(aminomethyl)-yl]-2-hydroxy-2-cyclohexyl-2-phenyl acetamide (Compound No. 45);

(1α,5α,6α)-N-[3-(4-pyridylmethyl)-3-azabicyclo[3.1.0]hexyl-6-(aminomethyl)-yl]-2-hydroxy-2-cyclohexyl-2-phenyl acetamide (Compound No. 46);

(1α,5α,6α)-N-[3-(2-pyridylmethyl)-3-azabicyclo[3.1.0]hexyl-6-(aminomethyl)-yl]-2-hydroxy-2-cyclohexyl-2-phenyl acetamide (Compound No. 47);

(1α,5α,6α)-N-[3-(4-pyridylmethyl)-3-azabicyclo[3.1.0]hexyl-6-(aminomethyl)-yl]-2-hydroxy-2-cyclopentyl-2-phenyl acetamide (Compound No. 48);

(1α,5α,6α)-N-[3-(3-pyridylmethyl)-3-azabicyclo[3.1.0]hexyl-6-(aminomethyl)-yl]-2-hydroxy-2,2-diphenyl acetamide (Compound No. 49);

(1α,5α,6α)-N-[3-(4-pyridylmethyl)-3-azabicyclo[3.1.0]hexyl-6-(aminomethyl)-yl]-2-hydroxy-2,2-diphenyl acetamide (Compound No. 50);

(1α,5α,6α)-N-[3-(2-pyridylmethyl)-3-azabicyclo[3.1.0]hexyl-6-(aminomethyl)-yl]-2-hydroxy-2,2-diphenyl acetamide (Compound NO. 51);

(1α,5α,6α)-N-[3-(2-pyridylmethyl)-3-azabicyclo[3.1.0]hexyl-6-(aminomethyl)-yl]-2-hydroxy-2-cyclopentyl-2-phenyl acetamide (Compound No. 52);

(1α,5α,6α)-N-[3-(3-pyridylmethyl)-3-azabicyclo[3.1.0]hexyl-6-(aminomethyl)-yl]-2-hydroxy-2-cyclopentyl-2-phenyl acetamide (Compound No. 53);

(1α,5α,6α)-N-[3-(3-methyl-2-butenyl)-3-azabicyclo[3.1.0]hexyl-6-(aminomethyl)-yl]-2-hydroxy-2-cyclopentyl-2-phenyl acetamide (Compound No. 54);

(1α,5α,6α)-N-[3-(3,4-methylenedioxyphenyl)methyl-3-azabicyclo[3.1.0]hexyl-6-(aminomethyl)-yl]-2-hydroxy-2-cyclopentyl-2-phenyl acetamide (Compound No. 55);

(1α,5α,6α)-N-[3-(3,4-methylenedioxyphenyl)methyl-3-azabicyclo[3.1.0]hexyl-6-(aminomethyl)-yl]-2-hydroxy-2-cyclohexyl-2-phenyl acetamide (Compound 56);

(1α,5α,6α)-[3-(4-methyl-3-pentenyl)-3-azabicyclo[3.1.0]hexyl-6-(methyl)-yl]-2-hydroxy-2-cyclohexyl-2-phenyl acetate L(+) tartrate salt (Compound 57);

(1α,5α,6α)-[3-(2-(3,4-methylenedioxyphenyl)ethyl)-3-azabicyclo[3.1.0]hexyl-6-(methyl)-yl]-2-hydroxy-2-cyclohexyl-2-phenyl acetate L(+) tartrate salt (Compound 58);

(1α,5α,6α)-[3-(1-phenylethyl)-3-azabicyclo[3.1.0]hexyl-6-(methyl)-yl]-2-hydroxy-2-cyclopentyl-2-phenyl acetate L(+) tartrate salt (Compound 59);

(1α,5α,6α)-N-[3-benzyl-3-azabicyclo[3.1.0]-hexyl-6-(aminomethyl)-yl]-2-hydroxy-2-cyclopentyl-2-phenyl acetamide hydrochloride salt (Compound No. 60);

(1α,5α,6α)-N-[3-benzyl-3-azabicyclo[3.1.0]-hexyl-6-(aminomethyl)-yl]-2-hydroxy-2-cyclopentyl-2-phenyl acetamide L(−) malic acid salt (Compound No. 61); and (1α,5α,6α)-N-[3-benzyl-3-azabicyclo[3.1.0]-hexyl-6-(aminomethyl)-yl]-2-hydroxy-2-cyclopentyl-2-phenyl acetamide maleate salt (Compound No. 62).

7. A pharmaceutical composition comprising a therapeutically effective amount of a compound as defined in claim 1, 2, 3, 4, 5 or 6 together with pharmaceutically acceptable carriers, excipients or diluents.

8. A method for treatment an animal or a human suffering from a disease or disorder of the respiratory, urinary and gastrointestinal systems, wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes or gastrointestinal hyperkinesis, comprising administering to said animal or human, a therapeutically effective amount of a compound having the structure of Formula I,

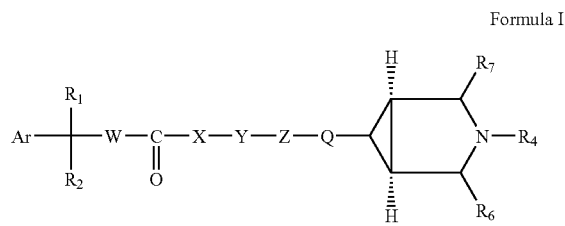

Formula I or its pharmaceutically acceptable salts, pharmaceutically acceptable enantiomers, diastereomers, N-oxides, wherein:
- Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) amino or N-lower alkyl ($C_1$-$C_4$) amino carbonyl;
- $R_1$ represents a hydrogen, hydroxy, hydroxy methyl, amino, alkoxy, carbamoyl or halogen (e.g. fluorine, chlorine, bromine and iodine);
- $R_2$ represents alkyl, $C_3$-$C_7$ cycloalkyl ring, a $C_3$-$C_7$ cyclo alkenyl ring, an aryl or a heteroaryl ring having 1 to 2 hetero atoms selected from a group consisting of oxygen, sulphur and nitrogen atoms; the aryl or a heteroaryl ring may be unsubstituted or substituted by one to three substituents independently selected from lower alkyl ($C_1$-$C_4$), lower perhalo alkyl ($C_1$-$C_4$), cyano, hydroxy, nitro, lower alkoxycarbonyl, halogen, lower alkoxy ($C_1$-$C_4$), lower perhalo alkoxy ($C_1$-$C_4$), unsubstituted amino, N-lower alkyl($C_1$-$C_4$)amino, N-lower alkyl($C_1$-$C_4$) amino carbonyl;
- W represents $(CH_2)_p$, where p represents 0 to 1;
- X represents an oxygen, sulphur, nitrogen or no atom;
- Y represents $CHR_5CO$ wherein $R_5$ represents hydrogen or methyl or $(CH_2)_q$ wherein q represents 0 to 4;
- Z represents oxygen, sulphur, $NR_{10}$, wherein $R_{10}$ represents hydrogen, $C_{1-6}$ alkyl;
- Q represents $(CH_2)_n$ wherein n represents 0 to 4, or $CHR_8$ wherein $R_8$ represents H, OH, $C_{1-6}$, alkyl, alkenyl alkoxy or $CH_2CHR_9$ wherein $R_9$ represents H, OH, lower alkyl ($C_1$-$C_4$) or lower alkoxy ($C_1$-$C_4$);
- $R_6$ and $R_7$ are indepedently selected from COOH, H, $CH_3$, $CONH_2$, $NH_2$, $CH_2NH_2$;
- $R_4$ represents $C_1$-$C_{15}$ saturated or unsaturated aliphatic hydrocarbon groups in which any 1 to 6 hydrogen atoms may be substituted with the group independently selected from halogen, arylalkyl, arylalkenyl, heteroarylalkyl or heteroarylalkenyl having 1 to 2 hetero atoms selected from a group consisting of nitrogen, oxygen and sulphur atoms with option that any 1 to 3 hydrogen atoms on the ring in said arylalkyl, arylalkenyl, hetero arylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkyl ($C_1$-$C_4$) amino, N-lower alkyl ($C_1$-$C_4$) amino carbonyl.

9. The method according to claim 8 for treatment of an animal or a human suffering from a disease or disorder of the respiratory, urinary and gastrointestinal systems, wherein the disease or disorder is, urinary incontinence, lower urinary tract symptoms (LUTS), bronchial asthma, chronic obstructive pulmonary disorders (COPD), pulmonary fibrosis, irritable bowel syndrome, obesity, diabetes or gastrointestinal hyperkinesis, comprising administering to said animal or human, a therapeutically effective amount of a compound having the structure of Formula II (Formula I when $R_6$ and $R_7$=H), its pharmaceutically acceptable salts, pharmaceutically acceptable enantiomers, diastereomers, N-oxides, wherein Ar, $R_1$, $R_2$, W, X, Y, Z, Q and $R_4$ are as defined for Formula I

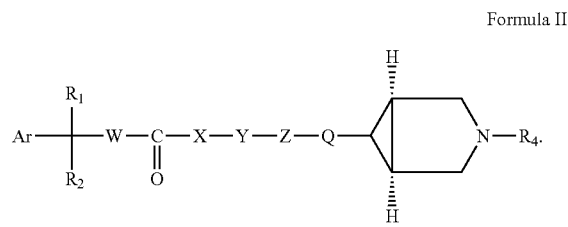

Formula II

10. The method according to claim 8 for treatment of an animal or a human suffering from a disease or disorder of the respiratory, urinary and gastrointestinal systems, wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes or gastrointestinal hyperkinesis, comprising administering to said animal or human, a therapeutically effective amount of a compound having the structure of Formula III [Formula I wherein W is $(CH_2)p$ where p=0, X is no atom and Y is $(CH_2)q$ where q=0, $R_6$=H, $R_7$=H] and its pharmaceutically acceptable salts, pharmaceutically acceptable enantiomers, diastereomers, N-oxides, wherein Ar, $R_1$, $R_2$, Z, Q and $R_4$ are as defined for Formula I

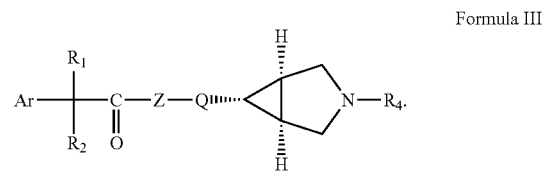

Formula III

11. The method according to claim 8 for treatment of an animal or a human suffering from a disease or disorder of the respiratory, urinary and gastrointestinal systems, wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes or gastrointestinal hyperkinesis, comprising administering to the said animal or human, a therapeutically effective amount of a compound having the structure of Formula IV (Formula I wherein W is $(CH_2)p$ where p=0, X is no atom and Y is $(CH_2)q$ where q=0, $R_6$=H, $R_7$=H and $R_2 = $ 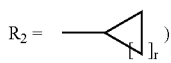

and its pharmaceutically acceptable salts, pharmaceutically acceptable enantiomers, diastereomers, N-oxides, wherein Ar, $R_1$, Z, Q and $R_4$ are as defined for Formula I, and r is 1 to 4

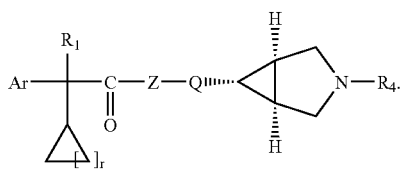

Formula IV

12. The method according to claim 8 for treatment of an animal or a human suffering from a disease or disorder of the respiratory, urinary and gastrointestinal systems, wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes or gastrointestinal hyperkinesis, comprising administering to said animal or human, a therapeutically effective amount of a compound having the structure of Formula V (Formula-I wherein W is $(CH_2)p$ where p=0, X is no atom and Y is $(CH_2)q$ where q=0, $R_6=H$, $R_7=H$, $R_2 = $ 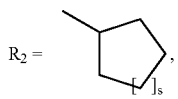

$R_1$ is hydroxy, Ar is phenyl), its pharmaceutically acceptable salts, pharmaceutically acceptable enantiomers, diastereomers, N-oxides, wherein $R_4$, Z and Q are the same as defined for Formula I, and s represents 1 to 2

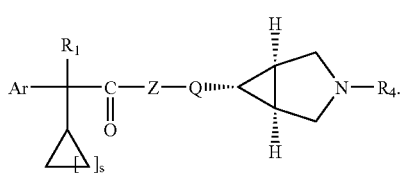

Formula V

13. The method for treatment of an animal or a human suffering from a disease or disorder of the respiratory, urinary and gastroinstestinal systems, wherein the disease or disorder is urinary incontinence, lower urinary tract symptoms (LUTS), bronchial asthma, chronic obstructive pulmonary disorders (COPD), pulmonary fibrosis, irritable bowel syndrome, obesity, diabetes or gastrointestinal hyperkinesis, comprising administering to said animal or human, a therapeutically effective amount of the pharmaceutical composition according to claim 7.

14. A process of preparing a compound of Formula I,

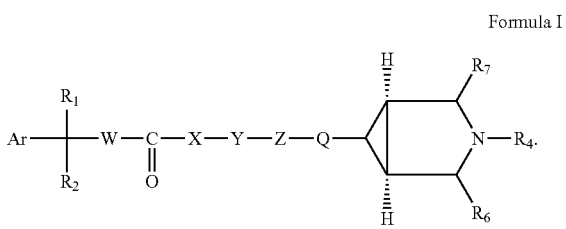

Formula I and its pharmaceutically acceptable salts, pharmaceutically acceptable enantiomers, diastereomers, N-oxides, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) amino or N-lower alkyl($C_1$-$C_4$) amino carbonyl;

$R_1$ represents a hydrogen, hydroxy, hydroxy methyl, amino, alkoxy, carbamoyl or halogen (e.g. fluorine, chlorine, bromine and iodine);

$R_2$ represents alkyl, $C_3$-$C_7$ cycloalkyl ring, a $C_3$-$C_7$ cyclo alkenyl ring, an aryl or a heteroaryl ring having 1 to 2 hetero atoms selected from a group consisting of oxygen, sulphur and nitrogen atoms; the aryl or a heteroaryl ring may be unsubstituted or substituted by one to three substituents independently selected from lower alkyl ($C_1$-$C_4$), lower perhalo alkyl ($C_1$-$C_4$), cyano, hydroxy, nitro, lower alkoxycarbonyl, halogen, lower alkoxy ($C_1$-$C_4$), lower perhalo alkoxy ($C_1$-$C_4$), unsubstituted amino, N-lower alkyl($C_1$-$C_4$)amino, N-lower alkyl($C_1$-$C_4$, amino carbonyl;

W represents $(CH_2)_p$, where p represents 0 to 1;

X represents an oxygen, sulphur, nitrogen or no atom;

Y represents $CHR_5CO$ wherein $R_5$ represents hydrogen or methyl or $(CH_2)q$ wherein q represents 0 to 4;

Z represents oxygen, sulphur, $NR_{10}$, wherein $R_{10}$ represents hydrogen, $C_{1-6}$ alkyl;

Q represents $(CH_2)_n$ wherein n represents 0 to 4, or $CHR_8$ wherein $R_8$ represents H, OH, $C_{1-6}$, alkyl, alkenyl alkoxy or $CH_2CHR_9$ wherein $R_9$ represents H, OH, lower alkyl ($C_1$-$C_4$) or lower alkoxy ($C_1$-$C_4$);

$R_6$ and $R_7$ are independently selected from COOH, H, $CH_3$, $CONH_2$, $NH_2$, $CH_2NH_2$;

$R_4$ represents $C_1$-$C_{15}$ saturated or unsaturated aliphatic hydrocarbon groups in which any 1 to 6 hydrogen atoms may be substituted with the group independently selected from halogen, arylalkyl, arylalkenyl, heteroarylalkyl or heteroarylalkenyl having 1 to 2 hetero atoms selected from a group consisting of nitrogen, oxygen and sulphur atoms with option that any 1 to 3 hydrogen atoms on the ring in said arylalkyl, arylalkenyl, hetero arylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkyl($C_1$-$C_4$) amino, N-lower alkyl ($C_1$-$C_4$) amino carbonyl, comprising (a) condensing a compound of Formula-VII with a compound of Formula VI

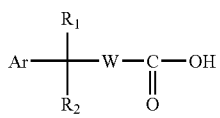

Formula VII

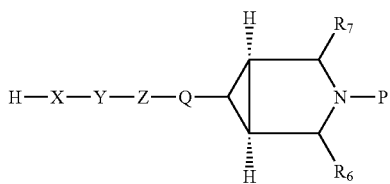

Formula VI wherein Ar, $R_1$, $R_2$, W, X, Y, Z, Q, $R_6$, and $R_7$ have the same meanings as defined earlier for Formula I, to give a protected compound of Formula VIII wherein Ar, $R_1$, $R_2$, W, X, Y, Z, Q, are the same as defined earlier and P is a protecting group for an amino group

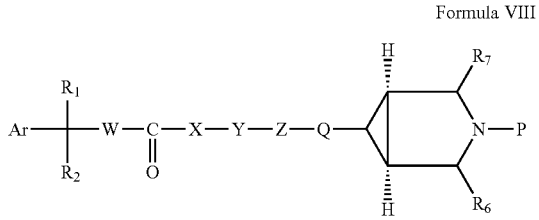

Formula VIII (b) deprotecting the compound of Formula VIII in the presence of a deprotecting agent to give an unprotected intermediate of Formula IX wherein Ar, $R_1$, $R_2$, W, X, Y, Z, and Q are the same as defined earlier,

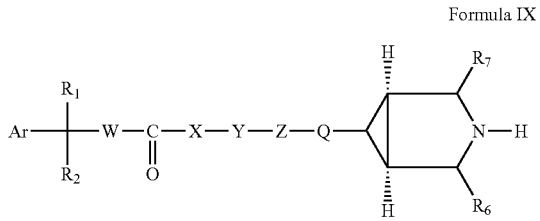

Formula IX (c) the intermediate of Formula IX is N-alkylated or benzylated with a suitable alkylating or benzylating agent to give a compound of Formula I wherein Ar, $R_1$, $R_2$, W, X, Y, Z, Q, $R_6$ and $R_7$ are the same as defined earlier.

15. The process according to claim 14 wherein P is any protecting group for an amino group and is selected from the group consisting of benzyl and t-butyloxy carbonyl groups.

16. The process according to claim 14 wherein the reaction of a compound of Formula VI with a compound of Formula VII to give a compound of Formula VIII is carried out in the presence of a condensing agent which is selected from the group consisting of 1-(3-dimethyl amino propyl)-3-ethyl carbodiimide hydrochloride (EDC) and 1,8-diazabicyclo [5.4.0] undec-7-ene (DBU).

17. The process according to claim 14 wherein the reaction of a compound of Formula VI with a compound of Formula VII to give a compound of Formula VIII is carried out in a suitable polar aprotic solvent selected from the group consisting of N,N-dimethylformamide, dimethyl sulfoxide, toluene, and xylene.

18. The process according to claim 14 wherein the reaction of compound of Formula VI with a compound of Formula VII is carried out at 0-140° C.

19. The process according to claim 14 wherein the deprotection of a compound of Formula VIII to give a compound of Formula IX is carried out with a deprotecting agent which is selected from the group consisting of palladium on carbon, trifluoroacetic acid (TFA) and hydrochloric acid.

20. The process according to claim 14 wherein the deprotection of a compound of Formula VIII to give a compound of Formula IX is carried out in a suitable organic solvent selected from the group consisting of methanol, ethanol, tetrahydrofuran and acetonitrile.

21. The process according to claim 14 wherein the N-alkylation or benzylation of a compound of Formula IX to give a compound of Formula I is carried out with a suitable alkylating or benzylating agent, L-$R_4$ wherein L is any leaving group and $R_4$ is the same as defined earlier.

22. The process according to claim 20 wherein the leaving group is selected from the group consisting of halogen, O-mestyl and O-tosyl groups.

23. The process according to claim 20 wherein the N-alkylation or benzylation of a compound of Formula IX to give a compound of Formula I is carried out in a suitable organic solvent selected from the group consisting of N,N-dimethylformamide, dimethyl sulfoxide, tetrahydrofuran and acetonitrile.

* * * * *